United States Patent [19]
Nobuyoshi et al.

[11] Patent Number: 5,250,069
[45] Date of Patent: Oct. 5, 1993

[54] CATHETER EQUIPPED WITH EXPANSIBLE MEMBER AND PRODUCTION METHOD THEREOF

[75] Inventors: Masakiyo Nobuyoshi, Kitakyusyu; Yoshiaki Sugiyama; Kyuuta Sagae, both of Fuji, all of Japan

[73] Assignee: Terumo Kabushiki Kaisha, Tokyo, Japan

[21] Appl. No.: 890,290

[22] Filed: May 26, 1992

Related U.S. Application Data

[63] Continuation of Ser. No. 809,219, Dec. 16, 1991, abandoned, which is a continuation of Ser. No. 432,775, Oct. 26, 1989, abandoned.

[30] Foreign Application Priority Data

| Feb. 27, 1987 | [JP] | Japan | 62-46195 |
| Mar. 3, 1987 | [JP] | Japan | 62-47977 |
| Nov. 5, 1987 | [JP] | Japan | 62-279698 |
| Nov. 5, 1987 | [JP] | Japan | 62-279699 |
| Jan. 15, 1988 | [JP] | Japan | 63-7231 |

[51] Int. Cl.$^5$ ............................................. A61M 29/04
[52] U.S. Cl. .................................... 606/192; 606/194; 604/96; 604/282
[58] Field of Search ................ 606/192, 194; 604/96, 604/282

[56] References Cited

U.S. PATENT DOCUMENTS 4,775,371 10/1988 Mueller .............................. 604/280

FOREIGN PATENT DOCUMENTS

| 0102422 | 3/1984 | European Pat. Off. |
| 2380786 | 9/1978 | France |
| 47-30891 | 12/1972 | Japan |
| 1566674 | 5/1980 | United Kingdom |

Primary Examiner—Michael H. Thaler
Attorney, Agent, or Firm—Frishauf, Holtz, Goodman & Woodward

[57] ABSTRACT

A catheter equipped with an expansible member for expanding a constricted portion inside a blood vessel, comprises an inner tube having a first lumen whose tip is open; an outer tube disposing coaxially with the inner tube, having the tip thereof at a position recessed by a predetermined length from the tip of the inner tube and forming a second lumen between it and the outer surface of the inner tube; a contractible or foldable expansible member having the tip portion fitted to the inner tube and the proximal portion fitted to the outer tube, and communicating with the second lumen near the proximal portion; a first opening communicating with the first lumen disposed at the proximal portion of the inner tube; a second opening communicating with the second lumen disposed at the proximal portion of the outer tube; and a rigidity imparting member disposed in at least one of the inner and outer tubes so as to extend in an axial direction. A method of production of an expansible member for use in a catheter equipped with an expansible member, comprises a step of forming a thermoplastic resin tube and heating an expansible member forming portion of this tube; a step of disposing the heated expansible member forming portion of the tube in an expansible member molding die the inner surface of which is formed in a shape obtainable when the expansible member is inflated; a step of bringing the heated expansible member forming portion of the tube disposed in the expansible member molding die into close contact with the inner surface of the molding die by pressurizing the inside of the tube; a step of cooling the expansible member forming portion of the tube; a step of removing the expansible member molding die from the tube; and a step of cutting the molded expansible member forming portion off the tube.

28 Claims, 17 Drawing Sheets

F I G. 11
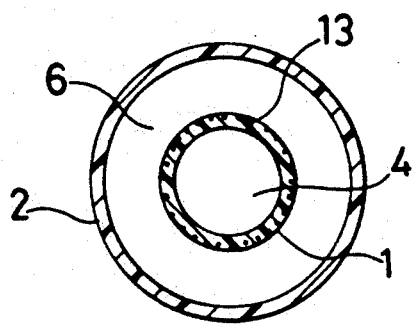
F I G. 12
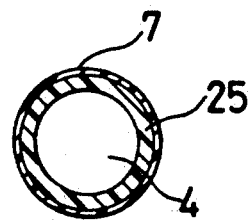
F I G. 13
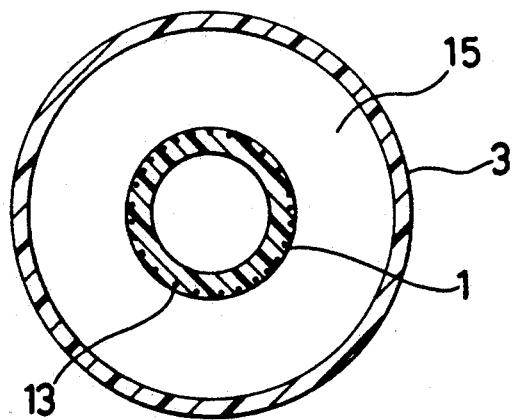

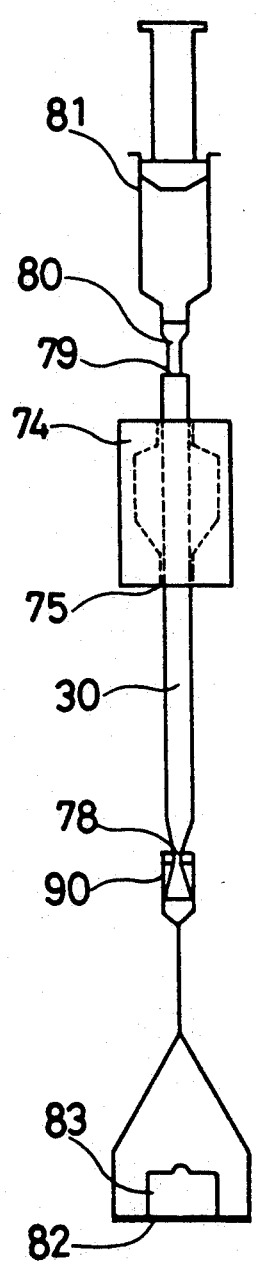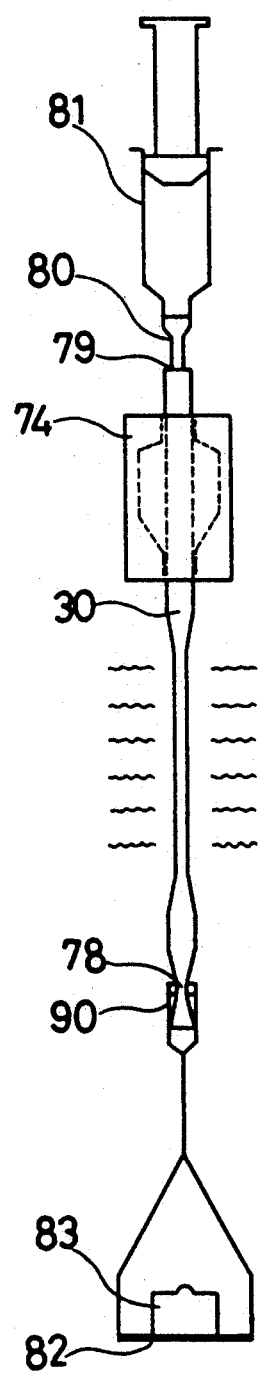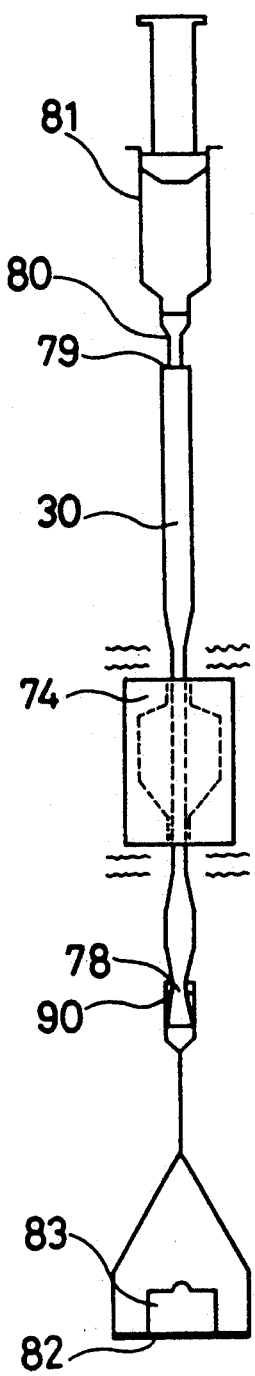

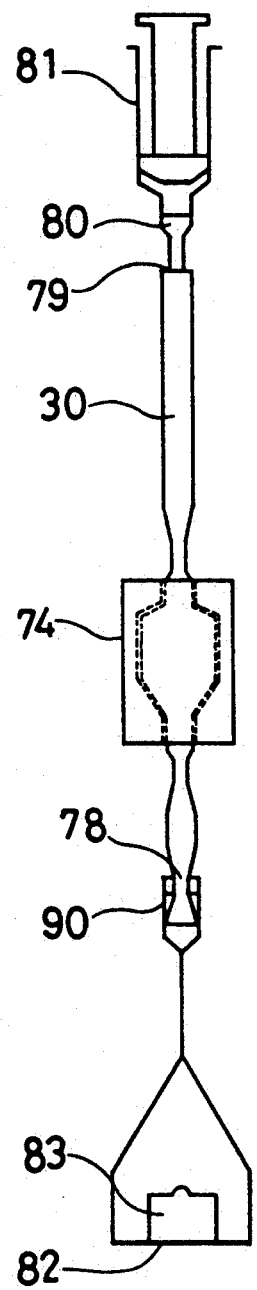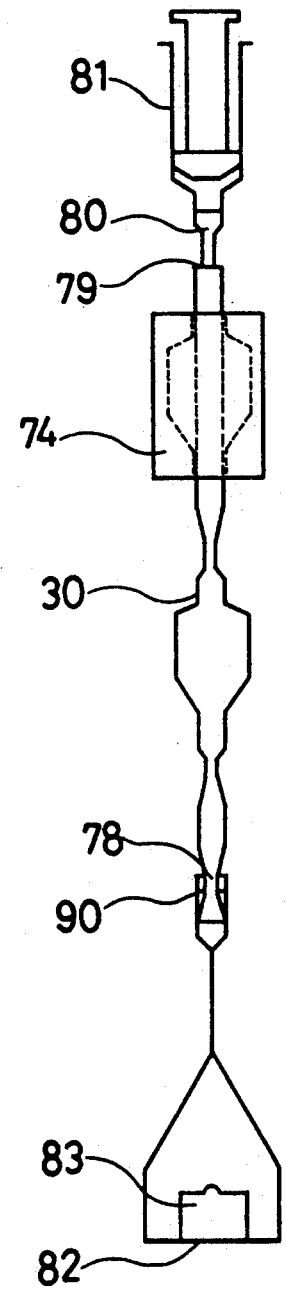
FIG. 26
FIG. 27

CATHETER EQUIPPED WITH EXPANSIBLE MEMBER AND PRODUCTION METHOD THEREOF

This application is a continuation of application Ser. No. 07/809,219, filed Dec. 16, 1991, (now abandoned), which is a continuation of Ser. No. 07/432,775, filed Oct. 26, 1989 (now abandoned).

TECHNICAL FIELD

The present invention relates to a catheter equipped with an expansible member used for the therapy of a stricture portion inside a blood vessel, as well as a production method thereof. In particular, the present invention relates to a catheter equipped with an expansible member for expanding a stricture portion inside a blood vessel thereby improving the blood flow on the periphery side of the stricture portion, as well as a production method thereof.

BACKGROUND ART

Heretofore, as a catheter equipped with an expansible member for expanding a stricture portion inside a blood vessel, there has been so-called Gruentich type disclosed, for example, in U.S. Pat. No. 4,195,637. Further, there has been used a so-called Simpson-Robert type as disclosed, for example, in U.S. Pat. No. 4,323,071.

Previously, adaptible cases for vasodilatation have been localized stricture near coronary artery from an anatomical point of view and it has been restricted, for example, to lesion of about 15-20 mm length, monobranched lesion, not-calcified lesion, etc. Then, for enlarging the range of the adaptible cases further, a catheter equipped with an expansible member of a low profile shape having the same structure but narrowed only at the tip has been considered in addition to the standard type of the above-mentioned type, which can be adaptible to the stricture in the peripheral blood vessel or to the severer stricture (sub-complete clogging).

The so-called Gruentich type catheter as described above is formed with a catheter tube having two lumens and an expansible member attached near the tip thereof. Then, one of the lumens opens at the tip of the catheter to constitute a channel for a guide wire and a tip pressure measurement. The other of the lumens is in communication with the inside of the expansible member on the base end thereof, to constitute a flow channel for a vasographic contrast media etc. under pressure, there expanding the expansible member. Then, the catheter is formed with flexible synthetic resin.

Further, the so-called Simpson-Robert type catheter has a coaxial double walled structure comprising an inner tube having a first lumen whose tip is open and an outer tube allowing the inner tube to be inserted to the inside thereof and, further, having an expansible member being attached to the tip thereof, in which a second lumen is formed between the inner surface of the outer tube and the outer surface of the inner tube. Then, an ultrafine metal pipe is disposed in the second lumen for removing bubbles. Also in the catheter of this type, like that the so-called Gruentich type, the catheter for the vasodilation of the blood vessel is made of a flexible synthetic resin.

As has been described above, the catheter is made of the flexible synthetic resin so that it can be inserted safely to the inside of the blood vessel. Since it is formed with the flexible synthetic resin, it can be inserted into the blood vessel and, moreover, gives less damages to the blood vessel walls. On the other hand, the flexibility may cause flection of the catheter during insertion into the blood vessel. Furthermore, for displacing and rotating the tip of the catheter in a delicate manner, the catheter is moved forward-to-backward or rotated in a delicate fashion at the proximal portion, thereby transmitting the torque to the tip. Further, for inserting the tip and, further, the expansible member of the catheter into the stricture portion of the blood vessel, the operation for enforcing the catheter is applied at the proximal portion of the catheter. However, there has been a drawback that the torque and the enforcing force are absorbed by the flexibility of the catheter and, thus, are less transmitted as far as the tip, to worsen the fine operationability.

In view of the above, the object of the present invention is to provide a catheter equipped with an expansible member with no risk of flection during insertion to the inside of the blood vessel, having high transmission efficiency of the torque and the enforcing force given to the proximal portion of the catheter and of excellent operationability.

Further, a conventional double-walled tube type catheter equipped with an expansible member, has been produced by forming the outer tube and the expansible member integrally and securing the tip of the expansible member on the extension of the outer tube to the tip of the inner tube.

Further, a so-called double-lumen catheter having a second lumen in the wall of a tubular member forming the catheter has been produced by inserting an extension tube from the tip to the inside of either one of the lumens of the tubular member, securing the tip of an expansible member to the tip of the extending tube, and securing the proximal portion of the expansible member to the tip of the double lumen catheter.

In addition, as a method of producing a catheter equipped with an expansible member for dilatating a stricture portion in an endotract, there has been a method of producing a catheter equipped with an expansible member referred to a Simpson-Robert type, for example, as disclosed in U.S. Pat. No. 4,411,055. According to the description of U.S. patent specification, an expansible member is disposed integrally to the tip of an outer tube forming a second lumen for fluid for expanding the expansible member between it and an inner tube whose tip is open for forming a first lumen, in which the expansible member is formed in the course of the production steps by closing the tip of the outer tube, heating the vicinity on the proximal portion of the closed portion and applying pressure from the proximal portion.

However, in the former method, since the expansible member is formed integrally with the outer tube, it has been difficult to provide the catheter and the expansible member with physical properties required respectively therefor. In addition, there has been a great possibility that the length and the thickness of the expansible member are not sufficiently made uniform and the reproducibility for the outer diameter of the expansible member upon expansion has not completely been satisfactory. Further, the latter method requires a step of fitting and securing an extending tube whose tip is open to the tip of one of the double lumens, which makes the operation complicate.

Further, in the conventional production method, it has also been difficult to form an expansible member of uniform wall thickness.

In view of the above, it is an object of the present invention to provide a method of producing a catheter equipped with an expansible member capable of optionally setting the length and the wall thickness of the expansible member, as well as easily producing a catheter equipped with an expansible member.

A further object of the present invention is to provide a method of producing an expansible member used for a catheter equipped with an expansible member, by which the length and the wall thickness of the expansible member can be made uniform and which can produce an expansible member with high reproducibility for the outer diameter of the expansible member upon inflation.

DISCLOSURE OF THE INVENTION

A catheter equipped with an expansible member according to the present invention comprises an inner tube having a first lumen whose tip is open, an outer tube disposed coaxially with the inner tube, having the tip thereof at a position recessed by a predetermined length from the tip of the inner tube and forming a second lumen between it and the outer surface of the inner tube, a contractible or foldable expansible member having a tip portion and a proximal portion, the proximal portion being fitted to the outer tube and the tip portion being fitted to the inner tube, and communicating with the second lumen near the proximal portion, a first opening communicating with the first lumen disposed at the proximal portion of the inner tube and a second opening communicating with the second lumen disposed at the proximal portion of the outer tube, and a rigidity imparting member disposed in at least one of the inner and outer tubes so as to extend in an axial direction.

A method of production of a catheter equipped with an expansible member according to the present invention comprises a step of forming an inner tube having a lumen which opens from the tip to the rear end, a step of forming an outer tube having a lumen which opens from the tip to the rear end and having an inner diameter larger than the outer diameter of the inner tube and being short by a predetermined length relative to the inner tube, a step of forming a contractible or foldable expansible member having a tip portion and a proximal portion, a step of inserting the inner tube into the outer tube, a step of securing the proximal portion of the expansible member to the tip of the outer tube and a step of securing the tip of the expansible member to the tip of the inner tube.

The method of producing an expansible member used for a catheter equipped with an expansible member according to the present invention comprises a step of forming a thermoplastic resin tube and then heating an expansible member forming portion of the tube, a step of disposing the heated expansible member forming portion of the tube in an expansible member molding die the inner surface of which is formed in a shape obtainable when the expansible member is inflated, a step of bringing the heated expansible member forming portion of the tube disposed in the expansible member molding die into close contact with the inner surface of the molding die by pressurizing the inside of the tube, a step of cooling the expansible member forming portion of the tube, a step of removing the expansible member molding die from the tube, and a step of cutting the molded expansible member portion of the tube.

BRIEF EXPLANATION OF THE DRAWINGS

FIG. 11 is a cross sectional view catheter equipped with the expansible member taken along line VI—VI in FIG. 6.

FIG. 12 is a cross sectional view of the catheter equipped with the expansible member taken along line VII—VII in FIG. 10.

FIG. 13 is a cross sectional view of the catheter equipped with the expansible member taken along line VIII—VIII in FIG. 10.

FIGS. 23, 24, 25, 26 and 27 are explanatory views for illustrating the steps for the method of producing an expansible member according to the present invention.

BEST MODE FOR PRACTICING THE INVENTION

Figure 1:
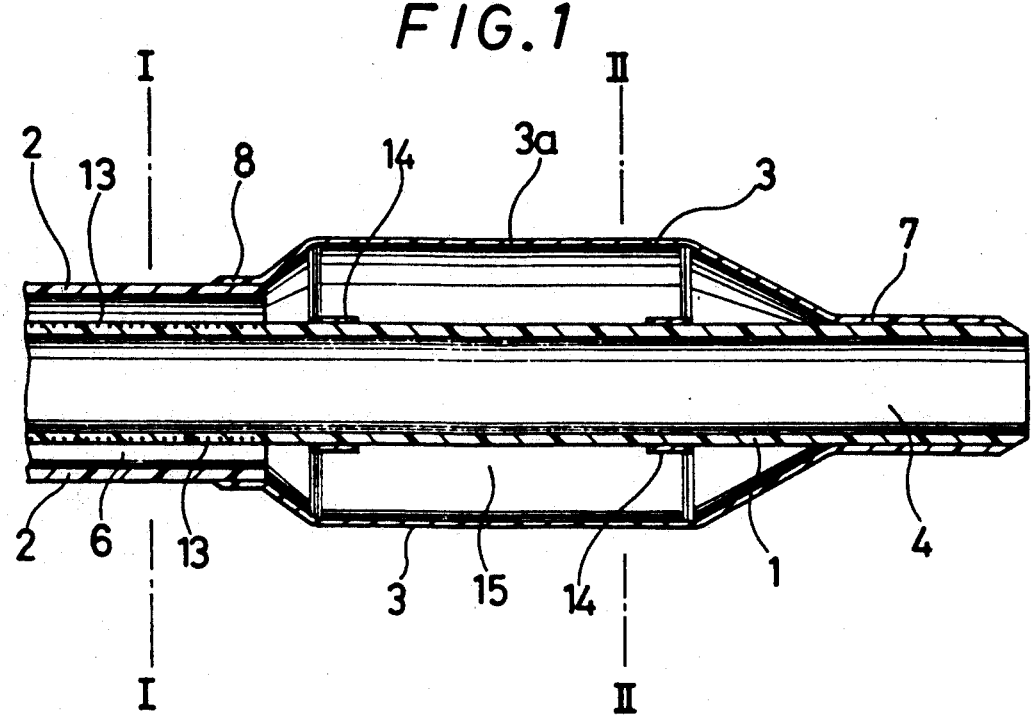
FIG. 1 is an enlarged cross sectional view for the tip portion of one embodiment of a catheter equipped with an expansible member according to the present invention.

A catheter equipped with an expansible member according to the present invention is to be explained referring to preferred embodiments shown in the drawings.

Figure 2:
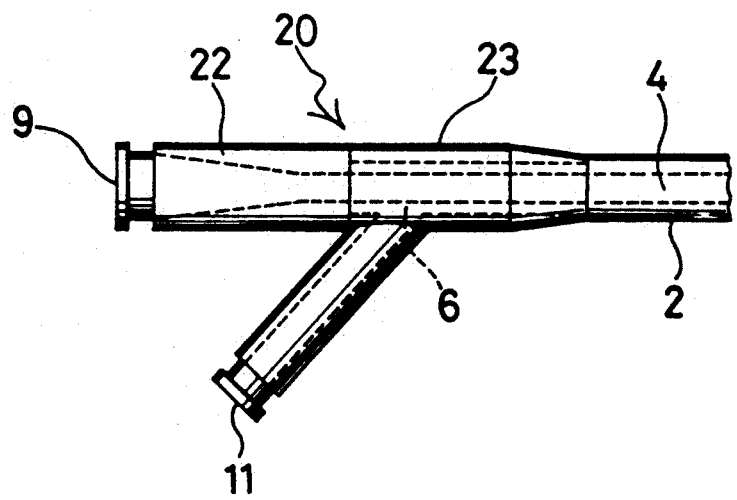
FIG. 2 is a view illustrating the proximal portion in one embodiment of a catheter equipped with an expansible member according to the present invention.

The catheter equipped with an expansible member according to the present invention, as shown in FIGS. 1 and 2, comprises an inner tube 1 having a first lumen 4 whose tip is opened, an outer tube 2 disposed coaxially with the inner tube 1, having the tip thereof at a position recessed by a predetermined length from the tip of the inner tube 1 and forming a second lumen 6 between it and the outer surface of the inner tube 1, a contractible or foldable expansible member 3 having a tip portion 7 and a proximal portion 8, the proximal portion 8 being fitted to the outer tube 2 while the tip portion 7 being fitted to the inner tube 1, and communicating with the second lumen 6 near the proximal portion, a first opening 9 disposed at the proximal portion of the inner tube 1 and communicating with the first lumen 4 and a second opening 11 disposed at the proximal portion of the outer tube 2 and communicating with the second lumen 6, and a rigidity imparting member 13 disposed in at least one of the inner tube 1 and the outer tube 2 so as to extend in an axial direction.

Explanation is to be made referring to the drawings.

The catheter equipped with an expansible member according to the present invention is formed with a catheter main body comprising the inner tube 1, the outer tube 2 and the expansible member 3, and a branched hub 20.

The inner tube 1 has the first lumen 4 opened at the tip. The first lumen 4 is a lumen for inserting a guide wire therethrough and in communication with the first opening 9 forming a guide wire port disposed to the branched hub 20 described later. The inner tube 1 has an outer diameter of 0.40 to 2.50 mm, preferably, 0.55 to 2.40 mm and an inner diameter of 0.25 to 2.35 mm, preferably, 0.30 to 1.80 mm.

Then, the diameter of the tip portion of the inner tube 1 is preferably reduced in a tapered shape toward the tip, because it can facilitate the insertion of the catheter into the blood vessel.

The material for forming the inner tube 1 preferably has a certain extent of flexibility and, for example, there can be used thermoplastic resin such as polyolefin such as polyethylene, polypropylene, ethylene-propylene copolymer and ethylene-vinyl acetate copolymer, polyvinyl chloride, polyamide elastomer, polyester and polyurethane, silicone rubber, latex rubber, etc., the thermoplastic resin being preferred and polyolefin being particularly preferred.

Further, the rigidity imparting member 13 is disposed to at least one of the inner tube 1 and the outer tube 2. In the embodiment shown in FIG. 1, the rigidity imparting member 13 is disposed to the inner tube 1. The rigidity imparting member 13 serves to prevent the flection of the catheter main body at the bent portion and, further, improve the torque transmission efficiency and the enforcing force of the catheter main body. By disposing the rigidity imparting member 13, flection of the catheter main body at the bent portion can be prevented. Further, when the catheter main body is rotated at the proximal portion of the catheter main body, the rotation can surely be transmitted as far as the tip portion, the operationability can be improved and introduction of the tip portion of the catheter into the highly strictured portion in the blood vessel is facilitated. Further, when the enforcing operation is applied to the catheter main body at the proximal portion of the catheter main body, the enforcing force can surely be transmitted to the tip portion, making it easy to insert the tip portion and the expansible member portion of the catheter into the stricture portion in the blood vessel.

Preferably, the rigidity imparting member 13 is disposed at least from the proximal end of the inner tube 1 as far as the vicinity at the tip portion of the outer tube 2. Further, the rigidity imparting member may also be disposed over the entire length of the inner tube 1. Further, for preventing the end portion of the rigidity imparting member from protruding beyond the tip of the catheter, the rigidity imparting member may not be disposed to the tip portion.

Figure 3:
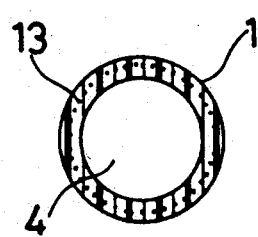
FIG. 3 is a cross sectional view for the inner tube of the catheter equipped with the expansible member shown in FIG. 1.

As the rigidity imparting member 13, a mesh-like rigidity imparting member is preferred. The mesh-like rigidity imparting member is preferably, a braided member formed with wire material, particularly, metal wire, as the metal wire, those metal wires, for example, made of stainless steels, elastic metals, super elastic alloys, shape memory alloys, etc. with the wire diameter of 0.01 to 0.2 mm, preferably, 0.03 to 0.1 mm may suitably be used. Then, the mesh-like rigidity imparting member can be formed by winding the metal wire as described above around the outer surface of the inner tube 1 in the mesh-like manner. Further, as shown in FIG. 3 representing the cross section of the inner tube 1, it is desirable that the rigidity imparting member disposed to the outer surface of the inner tube 1 is embedded to the outer surface of the inner tube 1 so as to make the outer surface smooth. This method can be applied be forming the inner tube 1 with a thermoplastic resin, winding the rigidity imparting member around the outer surface thereof, then, heating the inner tube 1 from the outside (for example, by inserting the inner tube through a heating dice) and embedding the rigidity imparting member to the outer surface of the inner tube. Further, the rigidity imparting member may also be formed by winding synthetic fibers such as polyamide, polyester, and polypropylene fibers as the wire material to the outer surface of the inner tube 1.

Figure 4:
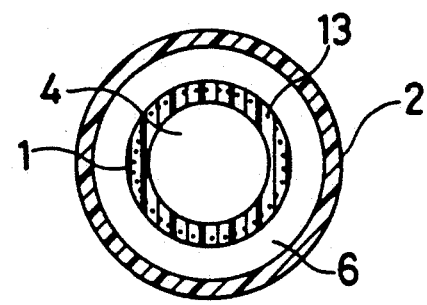
FIG. 4 is a cross section view of the catheter equipped the expansible member taken along line I—I in FIG. 1.

The outer tube 2 allows the inner tube 1 to be inserted therethrough and is disposed at such a position where the tip thereof is at a position recessed by a predetermined length from the tip of the inner tube. As shown in FIG. 4, which is a cross sectional view of the catheter equipped with the expansible member taken along line I—I in FIG. 1, a second lumen 6 is formed with the inner surface of the outer tube 2 and the outer surface of the inner tube 1. Thus, the second lumen constitutes a lumen having a sufficient volume. Then, the second lumen 6 is in communication at the tip thereof with the rear end at the inside of the expansible member 3. Further, the second lumen 6 is in communication at the rear end thereof with a second opening 11 of the branched hub 20 forming an injection port for injecting a fluid for inflating the expansible member (for example, vasographic contrast liquid).

As the material form forming the outer tube 2, those having a certain extent of flexibility are preferred and, for example, there can be used thermoplastic resin such as polyolefin such as polyethylene, polypropylene, ethylene-propylene copolymer and ethylene-vinyl acetate copolymer, polyvinyl chloride, polyamide elastomer, polyester and polyurethane, silicone rubber, latex rubber, etc., the thermoplastic resin being preferred and polyolefin being particularly preferred.

Further, the rigidity imparting member may be disposed to the outer tube 2 instead of disposing the rigidity imparting member to the inner tube 1. By disposing the rigidity imparting member, flection of the catheter main body at the bent portion can be prevented. Further, this can also increase the torque transmission efficiency of the catheter main body and, when the catheter main body is rotated at the proximal portion of the catheter main body, the rotation can surely be transmitted to the tip portion, the operationability can be improved, making it easy to introduce the tip portion, thus, the expanding member of the catheter to the highly stricture portion in the blood vessel. As the rigidity imparting member, those explained for the inner tube 1 can be used suitably. The outer tube 2 has an outer diameter of 0.75 to 4.30 mm, preferably, 1.00 to 4.00 mm and an inner diameter of 0.70 to 3.80 mm, preferably, 0.80 to 3.00 mm. Further, the difference between the outer diameter of the inner tube 1 and the inner diameter of the outer tube 2 is 0.30 to 3.40 mm, preferably, 0.50 to 1.20 mm.

Further, the rigidity imparting member may be disposed at least to either one of the inner tube 1 and the outer tube 2, and it may be disposed to both of the inner tube and the outer tube.

The expansible member 3 is contractible or foldable and it is contracted or folded at the outer circumference of the inner tube 1 in a state not inflated. Then, the expansible member 3 has such as portion at least partially made to a substantially cylindrical shape for enabling to inflate the stricture portion in the blood vessel, and the embodiment shown in FIG. 1 has a substantially cylindrical portion 3a having approximately equal diameter. The substantially cylindrical portion described above may or may not be a complete cylinder but it may be a polygonal cylindrical shape. Then, the proximal portion 8 of the expansible member 3 is secured in a liquid-tight manner to the tip portion of the outer tube 2 by means of adhesives or fusion. Further, the tip portion 7 is secured to the tip portion of the inner tube 1 also in a liquid-tight manner.

Figure 5:
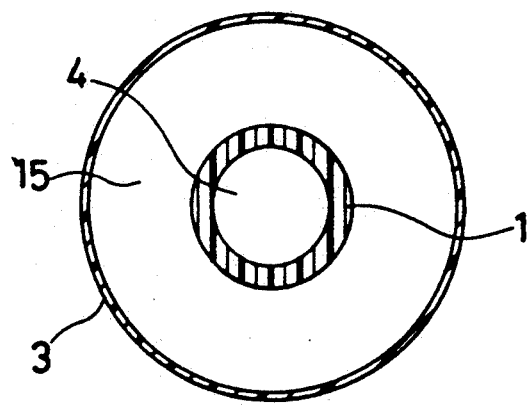
FIG. 5 is a cross sectional view of the catheter equipped with an expansible member taken along line II—II in FIG. 1.

Then, as shown in FIG. 5 representing the cross sectional view of the catheter equipped with an expansible member taken along line II—II in FIG. 1, the expansible member 3 forms an inflating space 15 betweeen the inner surface thereof and the outer surface of the inner tube 1. The inflating space 15 is in communication along the entire circumference at the proximal portion thereof with the second lumen 6. Thus, since the second lumen having a relatively large volume is in communication with the proximal end of the expansible member 3, injection of expanding fluid in the expansible member 3 from the second lumen is facilitated.

As the material for forming the expansible member 3, those having a certain extent of flexibility are preferred and there can be used, for example, thermoplastic resin such as polyolefin such as polyethylene, polypropylene, ethylene-propylene copolymer, ethylene-vinyl acetate copolymer and cross-linked ethylene-vinyl acetate copolymer, polyvinyl chloride, polyamide elastomer, polyester and polyurethane, silicon rubber, latex rubber, etc., the thermoplastic resin being preferred and the ecross-linked ethylene-vinyl acetate copolymer being particularly preferred.

Further, the forward and the backward portions of the cylindrical portion 3a of the expansible member 3 extended to the secured portions 7 and 8 with the inner tube 1 and the outer tube 2 are tapered.

As the size of the expansible member 3, the cylindrical portion, when inflated, has an outer diameter of 1.50 to 35.00 mm, preferably, 2.00 to 30.00 mm and a length of 10.00 to 80.00 mm, preferably, 15.00 to 75.00 mm. The entire length of the expansible member 3 is 15.00 to 120.00 mm, preferably, 20.00 to 100.00 mm.

Further, as shown in FIG. 1, it is preferred that markers 14 made of X-ray impermeable material (for example, make of gold, platinum or alloy thereof) are disposed to the outer surface of the inner tube 1, at a position nearer to the proximal end than the secured portion of expansible member 3 with the inner tube 1 and at a position nearer to the tip than the secured portion of the expansible member 3 with the outer tue 2, i.e., at the positions corresponding to both ends of the cylindrical portion 3a of the expansible member 3. This enables to easily confirm the position for the expansible member under X-ray perspection. As the form of the maker 14, a ring made of metal as described above may be attached by calking to the outer surface of the inner tube 1.

Further, in the catheter equipped with an expansible member according to the present invention, it is preferred for facilitating the insertion into the blood vessel and, further, into the guide catheter described later to apply hydrophilic treatment to a portion which is possibly brought in to contact with blood during use, that is, to the outer surface of the outer tube 2 and to the outer surface of the expansible member 3, so that the surfaces show lubricancy. As the hydrophilic treatment, there can be mentioned a method of coating a hydrophilic polymer, for example, poly(2-hydroxyethylmethacrylate), polyhydroxtyethylacrylate, hydroxypropylcellulose, methyl vinyl ether—maleic anhydride copolymer, polyethylene glycol, polyacrylamide and polyvinyl pyrrolidone.

As shown in FIG. 2, the branched hub 20 comprises an inner tube hub 22 and an outer tube hub 23. The inner tube hub 22 has a first opening 9 for forming a guide wire port and it is secured to the proximal portion of the inner tube 1. Further, the outer tube hub 23 has a second opening 11 for forming of an injection port, which is secured to the proximal portion of the outer tube 2. The inner tube hub 22 is secured to the outer tube hub 23 so as to seal the proximal portion of the outer tube hub 23.

As the material for forming the branched hub, there can be suitably used a thermoplastic resin such as polycarbonate, polyamide, polysulfone, polyarylate, methacrylate—butylene—styrene copolymer, etc. Further, instead of providing the branched hub, each of the first lumen and the second lumen may be attached, for example, with a tube having a port member disposed at the proximal end for forming an opening in a liquid seal manner.

Figure 6:
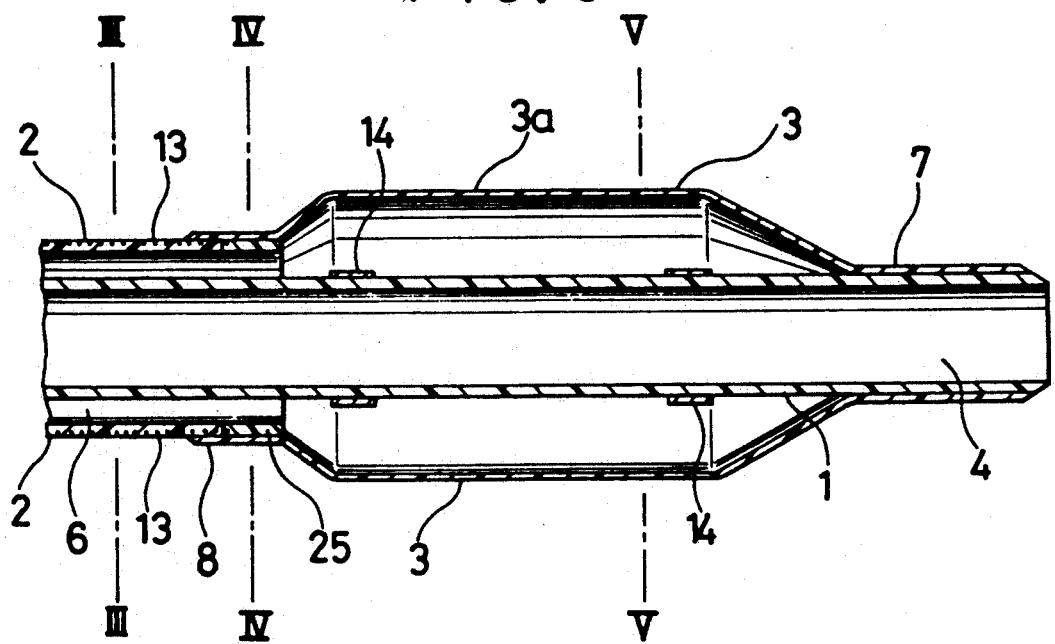
FIG. 6 is an enlarged cross sectional view for the tip portion of another embodiment of a catheter equipped with an expansible member according to the present invention.

Then, explanation is to be made for other embodiment of a catheter equipped with an expansible member according to the present invention shown in FIG. 6.

The catheter equipped with an expansible member of the embodiment shown in FIG. 6 comprises an inner tube 1 having a first lumen 4 whose tip is open an outer tube 2 disposed coaxially with the inner tube 1, having the tip thereof at a position recessed by a predetermined length from the tip of the inner tube 1 and forming a second lumen 6 between it and the outer surface of the inner tube 1, a contractible or foldable expansible member 3 having a tip portion 7 and a proximal portion 8 in which the proximal portion 8 is fitted to the outer tube 2 and the tip portion 7 is fitted to the inner tube 1, and communicating with the second lumen 6 near the proximal portion, a first opening communicating with the first lumen 4 disposed at the proximal portion of the inner tube 1 and a second opening 11 communicating with the second lumen 6 disposed at the proximal portion of the outer tube 2, the outer tube 2 having a rigidity imparting member extending in an axial direction and a portion not disposed within the rigidity imparting member at the tip thereof.

The catheter equipped with an expansible member of this embodiment is to be explained referred to the drawing mainly regarding the difference between it and the catheter equipped with the expansible member shown in FIG. 1.

The catheter equipped with the expansible member according to the present invention shown in FIG. 6 comprises a catheter main body having an inner tube 1, an outer tube 2 and an expansible member 3, a rigidity imparting member 13 formed to the outer tube 2 and an annular member 25 forming a portion not provided with the rigidity imparting member at the tip of the outer tube 2 having the rigidity imparting member, and a branched hub 20.

The inner tube 1 has a first lumen 4 whose tip is open. The first lumen 4 is a lumen for inserting a guide wire therethrough and communicating with a first opening 9 disposed to the branched hub 20 for forming the guide wire port shown in FIG. 2.

Then, the diameter at the tip of the inner tube 1 is preferably reduced in a tapered shape toward the side of the tip, since this facilitates the insertion of the catheter to the stricture portion inside the blood vessel. For the material and the size for forming the inner tube 1, those described above can be preferably used.

Figure 7:
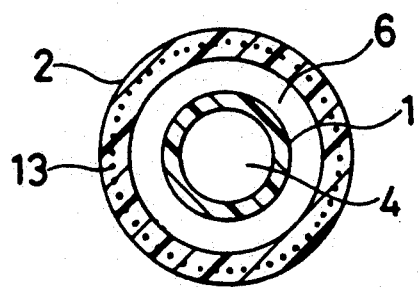
FIG. 7 is a cross sectional view of the catheter equipped with the expansible member taken along line III—III in FIG. 6.

The outer tube 2 allows the inner tube 1 to be inserted therethrough and a tip disposed at a position recessed somewhat from the tip of the inner tube. As shown in FIG. 7 which is a cross sectional view of the catheter equipped with the expansible member taken along line III—III in FIG. 6, the second lumen 6 is defined with the inner surface of the outer tube 2 and the outer surface of the inner tube 1. Thus, the second lumen 6 constitutes a lumen having a sufficient volume. Then, the second lumen 6 is in communication at the tip thereof with the rear end inside of the expansible member 3, while the proximal of the second lumen 6 is in communication with the second opening 11 of the branched hub 20 for forming an injection port for injecting a fluid (for example, vasographic contrast liquid) for inflating the expansible member. For the material and the size for forming the outer tube 2, those described previously are preferably used.

Further, the outer tube 2 is provided with the rigidity imparting member 13. As the rigidity imparting member 13, those as described previously can be used preferably.

Figure 8:
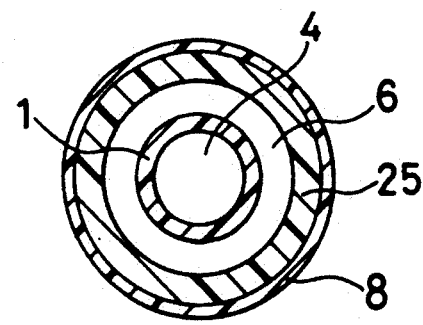
FIG. 8 is a cross sectional view of the catheter equipped with the expansible member taken along line IV—IV in FIG. 6.

Further, an annular member 25 is attached at the tip of the outer tube 2 having the rigidity imparting member 13, for forming a portion not provided with the rigidity imparting member 13. The annular member 25 is secured to the cut face at the tip of the outer tube 2 by means of fusion using heat, supersonic wave, high frequency wave, etc., bonding by using adhesive, solvent, etc. The annular member 25 serves to prevent the rigidity imparting member 13 from protruding externally out of the tip face of the outer tube 2 and also prevent the damage of the expansible member 3 due to the protruded portion of the rigidity imparting member. FIG. 7 is a cross sectional view of the catheter equipped with the expansible member taken along line III—III in FIG. 6, showing that the rigidity imparting member 13 is disposed to the outer tube 2. Further, FIG. 8 is a cross sectional view of the catheter equipped with the expansible member taken along line IV—IV in FIG. 6, showing that the annular member 25 disposed to the tip of the outer tube 2 is not provided with the rigidity imparting member. Accordingly, even if the inner surface of the expansible member 3 should be in contact with the tip of the outer tube 2 when the expansible member 3 described later is contracted or folded, since the member is in contact with the portion of the annular member 25 that is not provided with the rigidity imparting member, there is no worry that the expansible member 3 is damaged or destructed.

The annular member 25 may have any length so long as it has a length capable of covering the rigidity imparting member 13 protruding from the tip of the outer tube 2. However, if it is too long, since the portion has no rigidity imparting member and the torque transmission efficient is reduced, it is, preferably, less than about 10 mm and, more preferably, about 2 to 7 mm. As the material for forming the annular member 25, it is preferred that the material is identical or similar with that for the outer tube to be connected therewith. It is further preferred that the material is somewhat flexible and there can be used, for example, thermoplastic resin such as polyolefin such as polyethylene, polypropylene, ethylene-propylene copolymer and ethylene-vinyl acetate copolymer, polyvinyl chloride, polyamide elastomer, polyester and polyurethane, silicon rubber, latex rubber, etc., the thermoplastic resin being preferred and polyolefin being more preferred.

The method of forming a portion not disposed with the rigidity imparting member 13 to the tip of the outer tube 2 having the rigidity imparting member 13 may be conducted by a method other than using the annular member described above. For instance, for forming the rigidity imparting member at the outer surface from a position somewhat distant from the tip of the outer tube to the rear end of the outer tube formed with the thermoplastic resin, metal wires such as made of stainless steel, elastic metal, superelastic alloy, shape memory alloy, etc. may be wound as wire material in a mesh-like manner and, further, the outer tube 2 wound around with the metal wire may be heated from the outside (for example, by inserting the outer tube through the heating dice), so that the rigidity imparting member is embedded in the outer wall of the outer tube 2, thereby forming a portion not having the rigidity imparting member at the tip. Further, a resin which is adhesive to the material for forming the outer tube 2 may be coated to the tip of the outer tube 2 at such a thickness that the rigidity imparting member situated at the tip does not protrude to the outside, thereby forming a portion having no rigidity imparting member.

Figure 9:
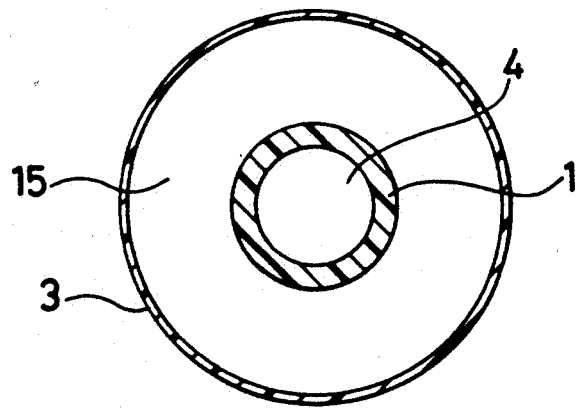
FIG. 9 is a cross sectional view of the catheter equipped with the expansible member taken along line V—V in FIG. 6.

The expansible member 3 is contractible or foldable, and, in a state not-inflated, it is contracted or folded to the outer circumference of the inner tube 1. Then, the expansible member 3 at least has a portion of substantially cylindrical shape for easily dilatating the stricture portion of the blood vessel and the embodiment shown in FIG. 6 has substantially cylindrical portion 3a of about equal diameter. The substantially cylindrical portion may not always be a complete cylinder but it may be a polygonal cylinder. Then, the expansible member 3 is secured at the proximal portion 8 to the tip of the outer tube 2 by means of adhesive or heat fusion in a liquid-tight manner, while the tip 7 thereof is secured in the same manner as that for the tip of the inner tube 1 in a liquid-tight manner. As shown in FIG. 9 which is a cross sectional view of the catheter equipped with the expansible member taken along line V—V in FIG. 6, the expansible member 3 forms an inflating space 15 between the inner surface of the expansible member 3 and the outer surface of the inner tube 1. The inflating space 15 is in communication with the second lumen 6 at the entire circumference of the rear end portion. Thus, since the second lumen having a large volume is in communication with the rear end of the expansible member 3, expanding fluid can easily be injected from the second lumen to the inside of the expansible member 3. As the material and the size for forming the expansible member 3, those described above can be used suitably. Further, the portions of the expansible member 3 from the front and rear of the cylindrical portion 3a to the portions 7 and 8 secured with the inner tube 1 and outer tube 2 are tapered.

Further, it is preferred that markers 14 made of X-ray impermeable material (for example, gold, platinum or alloys thereof) are disposed to the outer surface of the inner tube 1, at the position nearer to the rear end from the securing portion between the expansible member 3 and the inner tube 1, and at the position nearer to the tip from the secured portion between the expansible member 3 and the inner tube 2, that is, at the both ends of the cylindrical portion 3a of the expansible member 3.

Further, in the catheter equipped with the expansible member according to the present invention, it is preferred to apply hydrophilic treatment to those portions possibly being brought into contact with blood upon use, that is, to the outer surface of the outer tube 2 and the outer surface of the expansible member 3 for facilitating the insertion into the blood vessel and, further, into the guide catheter described later, so that they exhibit lubricancy when brought into contact with blood, etc. As for the hydrophilic treatment, those described previously can be used suitably.

The branched hub 20 is identical with that explained referring to FIG. 2.

Figure 10:
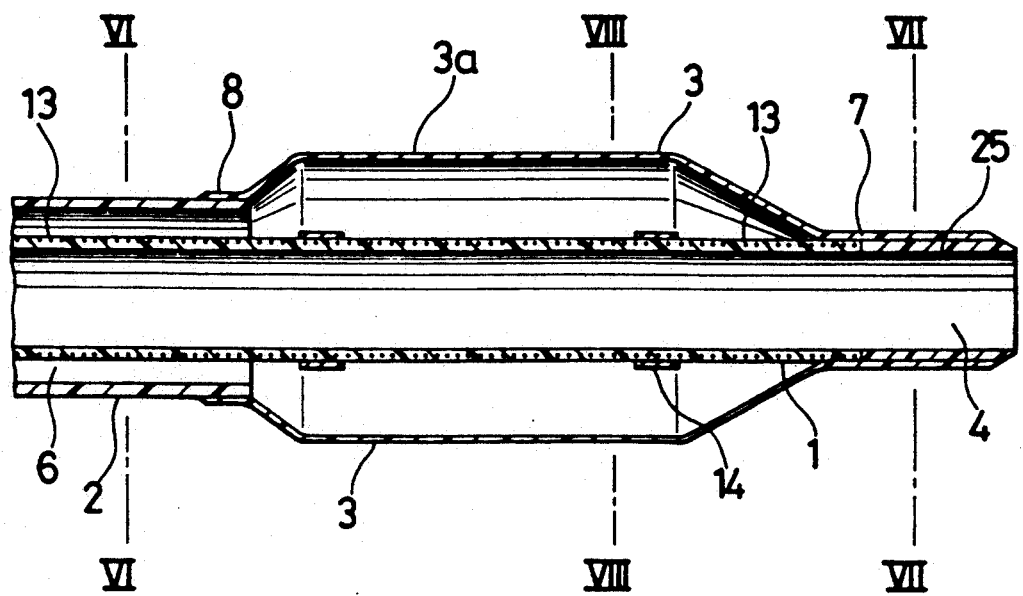
FIG. 10 is an enlarged cross sectional view for the tip portion of another embodiment of a catheter equipped with an expansible member according to the present invention.

Then, explanation is to be made for other embodiment of a catheter equipped with an expansible member according to the present invention shown in FIG. 10.

The catheter equipped with an expansible member of the embodiment shown in FIG. 10 comprises an inner tube 1 having a first lumen 4 whose tip is open, an outer tube 2 disposed coaxially with the inner tube 1, having the tip thereof at a position recessed by a predetermined length from the tip of the inner tube 1 and forming a second lumen 6 between it and the outer surface of the inner tube 1, a contractible or foldable expansible member 3 having a tip portion 7 and a proximal portion 8 in which the proximal portion 8 is fitted to the outer tube 2 and the tip portion 7 is fitted to the inner tube 1, and communicating with the second lumen 6 near the proximal portion, a first opening 9 communicating with the first lumen 4 disposed at the proximal portion of the inner tube 1, a second opening 11 communicating with the second lumen 6 disposed at the proximal portion of the outer tube 2, the inner tube 1 having a rigidity imparting member extending from the proximal to the tip in an axial direction and a portion not disposed with the rigidity imparting member at the tip thereof.

The embodiment of the catheter equipped with the expansible member according to the present invention shown in FIG. 10 comprises a catheter main body having an inner tube 1, an outer tube 2 and an expansible member 3, a rigidity imparting member 13 formed to the inner tube 1 and an annular member 25 forming a portion not provided with the rigidity imparting member at the tip of the inner tube 1 having the rigidity imparting member, and a branched hub 20.

The inner tube 1 has a first lumen 4 whose tip is open. The first lumen 4 is a lumen for inserting a guide wire therethrough and communicating with a first opening 9 disposed to the branched hub 20 for forming the guide wire port shown in FIG. 2.

Then, the diameter at the tip of the inner tube 1 is preferably reduced in a tapered shape toward the side of the tip, since this facilitates the insertion of the catheter to the stricture portion inside the blood vessel. For the material and the size for forming the inner tube 1, those described above can be preferably used.

Further, the inner tube 1 is provided with the rigidity imparting member 13. Further, an annular member 25 is attached at the tip of the outer tube 2 having the rigidity imparting member 13, for forming a portion not provided with the rigidity imparting member 13. As the rigidity imparting member 13, those as described previously can be used preferably. The annular member 25 is secured to the cut face at the tip of the inner tube 1 by means of fusion using heat, supersonic wave, high frequency wave, etc., bonding by using adhesive, solvent, etc. for serving to prevent the rigidity imparting member 13 from protruding externally out of the tip face of the inner tube 1. FIG. 11 is a cross sectional view of the catheter equipped with the expansible member taken along line VI—VI in FIG. 10, showing that the rigidity imparting member 13 is disposed to the inner tube 1. Further, FIG. 12 is a cross sectional view of the catheter equipped with the expansible member taken along line VII—VII in FIG. 10, showing that the annular member 25 disposed to the tip of the inner tube 1 is not provided with the rigidity imparting member. The annular member 25 may have any length so long as it has a length capable of covering the rigidity imparting member 13 protruding from the tip of the inner tube 1. However, if it is too long, since the portion has no rigidity imparting member and the torque transmission efficient is reduced, it is, preferably, less than about 10 mm and, more preferably, about 2 to 7 mm. As the material for forming the annular member 25, it is preferred that the material is identical or similar with that for the inner tube to be connected therewith. It is further preferred that the material is somewhat flexible and there can be used, for example, thermoplastic resin such as polyolefin such as polyethylene, polypropylene, ethylene—propylene copolymer and ethylene—vinyl acetate copolymer, polyvinyl chloride, polyamide elastomer, polyester and polyurethane, silicone rubber, latex rubber, etc., the thermoplastic resin being preferred and polyolefin being more preferred.

Thus, even if the rigidity imparting member 13 is disposed to the inner tube 1, since the tip portion thereof forms a portion not having the rigidity imparting member, the rigidity imparting member does not protrude from the end face at the tip of the inner tube when advancing in a blood vessel thereby preventing the damage to the inner wall of the blood vessel. Then, it is preferred that the diameter of the annular member 25 as the tip of the inner tube 1 forming the portion not having the rigidity imparting member 13 is reduced in a tapered shape toward the tip, since this facilitates the insertion of the catheter into the blood vessel. Further, it is preferred that the rigidity imparting member 13 disposed to the inner tube 1 is extended to a portion corresponding to the contractible or foldable portion of the expansible member 3 (portion excluding the proximal portion secured to the outer tube 2 and the tip portion secured to the inner tube 1) from the proximal portion of the inner tube 1. Such disposition can prevent the inner tube 1 from reflexing in the portion of the expansible member thereby enabling to prevent the destruction of the expansible member caused by reflexing, as well as transmit the torque and enforcing force reliably to the tip of the inner tube 1.

The method of forming a portion not disposed with the rigidity imparting member 13 to the tip of the inner tube 1 having the rigidity imparting member 13 may be conducted by a method other than using the annular member described above. For instance, for forming the rigidity imparting member at the outer surface from a position somewhat distant from the tip of the inner tube to the rear end of the inner tube formed with the thermoplastic resin, metal wires such as made of stainless steel, elastic metal, superelastic alloy, shape memory alloy, etc. may be wound as wire material in a mesh-like manner and, further, the inner tube wound around with the metal wire may be heated from the outside (for example, by inserting the outer tube through the heating dice), so that the rigidity imparting member is embedded in the outer wall of the inner tube, thereby forming a portion not having the rigidity imparting member at the tip. Further, a resin which is adhesive to the material for forming the inner tube may be coated to the tip of the inner tube 1 at such a thickness that the rigidity imparting member situated at the tip of the inner tube does not protrude to the outside, thereby forming a portion having no rigidity imparting member.

The outer tube 2 allows the inner tube 1 to be inserted therethrough and is disposed at such a position where the tip thereof is at a position recessed by a predetermined length from the tip of the inner tube. As shown in FIG. 11, which is a cross sectional view taken along line VI—VI in FIG. 10, a second lumen 6 is formed with the inner surface of the outer tube 2 and the outer surface of the inner tube 1. Then, the second lumen 6 is in communication at the tip thereof with the rear end at the inside of the expansible member 3, and the second lumen 6 is in communication at the rear end thereof with a second opening 11 of the branched hub 20 forming an injection port for injecting a fluid for inflating the expansible member (for example, vasographic contrast liquid).

As the material for forming the outer tube 2, those described above can suitably be used.

The expansible member 3 is contractible or foldable, and, in a state not-inflated, it is contracted or folded to the outer circumference of the inner tube 1. Then, the expansible member 3 at least has a portion of substantially cylindrical shape for easily dilatating the stricture portion of the blood vessel and the embodiment shown in FIG. 10 has substantially cylindrical portion 3a of about equal diameter. The substantially cylindrical portion may not always be a complete cylinder but it may be a polygonal cylinder. Then, the expansible member 3 is secured at the proximal portion 8 to the tip of the outer tube 2 by means of adhesive or heat fusion in a liquid-tight manner. The tip portion 7 is secured in the same manner to the tip of the inner tube 1 in a liquid-tight manner. As shown in FIG. 13 which is a cross sectional view of the catheter equipped with the expansible member taken along line VIII—VIII in FIG. 10, the expansible member 3 forms an inflating space 15 between the inner surface of the expansible member 3 and the outer surface of the inner tube 1. The inflating space 15 is in communication with the second lumen 6 at the entire circumference of the proximal portion. Thus, since the second lumen having a large volume is in communication with the rear end of the expansible member 3, expanding fluid can easily be injected from the second lumen to the inside of the expansible member 3. As the material and the size for forming the expansible member 3, those described above can be used suitably. Further, the portions of the expansible member 3 from the front and rear of the cylindrical portion 3a to the portions 7 and 8 secured with the inner tube 1 and outer tube 2 are tapered.

Further, it is preferred that markers 14 made of X-ray impermeable material (for example, gold, platinum or alloys thereof) are disposed to the outer surface of the inner tube 1, at the position nearer to the rear end from the securing portion between the expansible member 3 and the inner tube 1, and at the position nearer to the tip from the secured portion between the expansible member 3 and the outer tube 2, that is, at the both ends of the cylindrical portion 3a of the expansible member 3.

Further, in the catheter equipped with the expansible member according to the present invention, it is preferred to apply hydrophilic treatment to those portions possibly being brought into contact with blood upon use, that is, to the outer surface of the outer tube 2 and the outer surface of the expansible member 3 for facilitating the insertion into the blood vessel and, further, into the guide catheter described later, so that they exhibit lubricancy when brought into contact with blood, etc. As for the hydrophilic treatment, those described previously can be used suitably.

The branched hub 20 is identical with that explained referring to FIG. 2.

Then, the method of producing a catheter equipped with an expansible member according to the present invention is to be explained referring to the drawings.

The method of producing the catheter equipped with the expansible member according to the present invention comprises a step of forming an inner tube having a lumen opened from the tip to the rear end, a step of forming an outer tube having a lumen opened from the tip to the rear end, with the inner diameter being larger than the outer diameter of the inner tube and shorter by a predetermined length than the inner tube, a step of forming a contractible or foldable expansible member having a tip portion and a proximal portion, a step of inserting the inner tube to the inside of the outer tube, a step of securing the proximal portion of the expansible member to the tip portion of the outer tube and a step of securing the tip portion of the expansible member to the tip portion of the inner tube.

Then, each of the steps is to be explained referring to the catheter equipped with the expansible member shown in FIG. 1.

The step of forming inner tube 1 having the first lumen 4 communicating from the tip to the rear end can be conducted using flexible material, for example, thermoplastic resin such as polyolefin such as polyethylene, polypropylene, ethylene—propylene copolymer and ethylene—vinyl acetate copolymer, polyvinyl chloride, polyamide elastomer, polyester and polyurethane, silicon rubber or latex rubber by means of extrusion molding followed by cutting to a predetermined length, or injection molding, dipping, etc.

The inner tube 1 has a length of 300 to 2100 mm, preferably, 400 to 1350 mm, an outer diameter of 0.40 to 2.50 mm, preferably, from 0.55 to 2.40 mm and inner diameter of 0.25 to 2.35 mm, preferably, 0.30 to 1.80 mm.

Further, it is preferred to provide the thus formed inner tube 1 with a rigidity imparting member 13 for preventing the flection of the catheter main body at the bent portion and, further, for improving the torque transmission efficiency of the catheter main body. The rigidity imparting member can be formed easily by a method, for example, of applying wire material to the outer surface of the inner tube 1 in a mesh-like manner.

Figure 14:
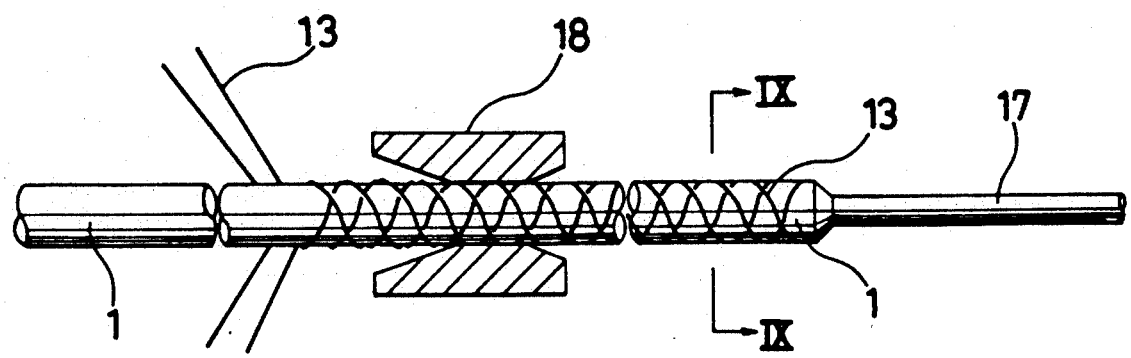
FIG. 14 is an explanatory view for the method of applying a rigidity imparting member over the inner tube in the method of producing a catheter equipped with an expansible member in accordance with the present invention.
Figure 15:
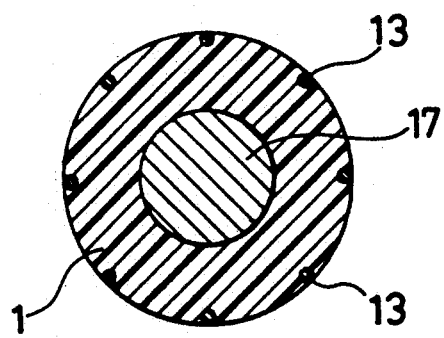
FIG. 15 is a cross sectional view taken along line IX—IX in FIG. 14.

As the wire material, metal wire is preferred and, for example, stainless steel, elastic metal, superelastic alloy or shape memory alloy with a wire diameter of 0.01 to 0.2 mm, preferably, 0.03 to 0.1 mm is preferred. Further, it is preferred that the rigidity imparting member 13 disposed to the outer surface of the inner tube 1 is embedded in the outer surface of the inner tube 1 so as to make the outer surface of the inner tube 1 smooth. This method can be applied, for example, by inserting a core metal 17 through the inner tube 1 formed with a thermoplastic resin and then inserting the inner tube 1 into a heating dice 18 while winding the rigidity imparting member 13 over the inner tube 1 as shown in FIG. 14. Then, in the portion passed through the inside of the heating dice 18, the rigidity imparting member 13 is embedded in the outer surface of the inner tube 1 as shown in FIG. 15 which is a cross sectional view taken along line IX—IX in FIG. 14. Further, although the inner tube 1 is caused to pass through the heating dice while winding the rigidity imparting member therearound in the previous explanation, the method is not restricted only thereto but the rigidity imparting member may previously be applied over the outer surface of the inner tube which is then inserted through the heating dice.

Further, the rigidity imparting member 13 may be formed by winding, as the wire material, synthetic fibers such as polyamide fibers, polyester fibers or polypropylene fibers to the outer surface of the inner tube 1. As used herein, the term "wire material" for the rigidity imparting members 13 comprises not only metal material, but also synthetic fiber material.

Further, it is preferred to apply coating of a thermoplastic resin to the outer surface of the inner tube 1 in which the rigidity imparting member is embedded and, as the thermoplastic resin, there can be suitably used thermoplastic resin such as polyolefin such as polyethylene, polypropylene, ethylene—propylene copolymer and ethylene—vinyl acetate copolymer, polyvinyl chloride, polyurethane and polyester. It is more preferable to use those materials having high adhesiveness to the outer surface of the inner tube 1, for example, the material identical with or similar to that used for forming the inner tube 1. The thermoplastic resin can be coated easily by a method of inserting the inner tube 1, in which the rigidity imparting member is deposited and embedded, through a dice that discharges a coating thermoplastic resin in a molten state.

Then, it is preferred that the diameter at the tip portion of the inner tube 1 is reduced toward the tip in a tapered shape, because this can facilitate the insertion of the catheter into a blood vessel. The fabrication to the tip of the inner tube may be applied after attaching an expansible member 3 described later.

Then, the step of forming the outer tube 2 having the second lumen 6 communicating the tip to the rear end can be applied to using the same flexible material as that for the inner tube 1, for example, thermoplastic resin such as polyolefin such as polyethylene, polypropylene, ethylene—propylene copolymer and ethylene—vinyl acetate copolymer, polyvinyl chloride, polyamide elastomer, polyester and polyurethane, silicone rubber or latex rubber by means of extrusion molding followed by cutting to a predetermined length, injection molding or dipping.

The outer tube 2 has a length of 200 to 2000 mm, preferably, 250 to 1450 mm, an outer diameter of 0.75 to 4.30 mm, preferably, 1.00 to 4.00 mm, and inner diameter of 0.70 to 3.80 mm, preferably, 0.80 to 3.00 mm. The difference between the outer diameter of the inner tube 1 and the inner diameter of the outer tube 2 is from 0.30 to 3.40 mm, preferably, 0.50 to 1.20 mm.

Further, instead of disposing the rigidity imparting member to the inner tube 1, the rigidity imparting member may be disposed to the outer tube. As the method of forming the rigidity imparting member, the method as explained for the step of forming the inner tube 1 can suitably be utilized. In particular, in a case of disposing the rigidity imparting member to the outer tube, since the outer tube is liable to be in contact with the inner surface of a blood vessel and, in order to reduce the onset of thrombus, it is preferred that the rigidity imparting member disposed to the outer surface of the outer tube is embedded in the outer surface of the outer tube to make the outer surface smooth. For this method, the method as explained for the step of forming the inner tube 1 can also suitably be used. Further, for making the outer surface of the outer tube more smooth, it is preferred to apply a coating of a thermoplastic resin to the outer surface of the outer tube 2 embedded with the rigidity imparting member. As the thermoplastic resin and the method of coating the same, those explained for the inner tube 1 can suitably be used. The steps of forming the inner tube and the outer tube may be conducted in any order or conducted simultaneously.

Then, explanation is to be made for the step of forming the contractible or foldable expansible member having the tip portion and the proximal portion.

Figure 19:
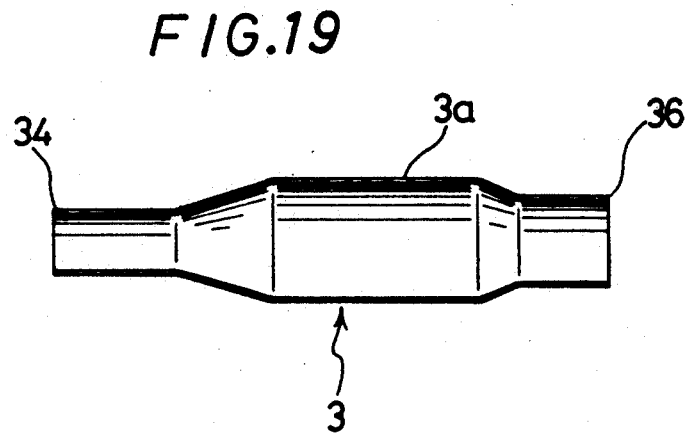

The expansible member 3 is contractible or foldable and, in a state not-inflated, it can be contracted or folded to the outer circumference of the inner tube 1. Then, the expansible member 3 has a substantially cylindrical portion 3a at least a portion of which is substantially cylindrical for easily dilatating the stricture portion of a blood vessel, as shown in FIG. 19. The substantially cylindrical portion may not always be a completely circular cylinder but it may be a polygonal cylinder.

The expansible member 3 preferably has flexibility and can be formed, for example, by using thermoplastic resin such as polyolefin such as polyethylene, polypropylene, ethylene—propylene copolymer, ethylene—vinyl acetate copolymer and cross-linked ethylene—vinyl acetate copolymer, polyvinyl chloride and polyurethane, more preferably, cross-linked ethylene—vinyl acetate copolymer, for example, as shown in FIG. 16 through FIG. 19.

Figure 16:
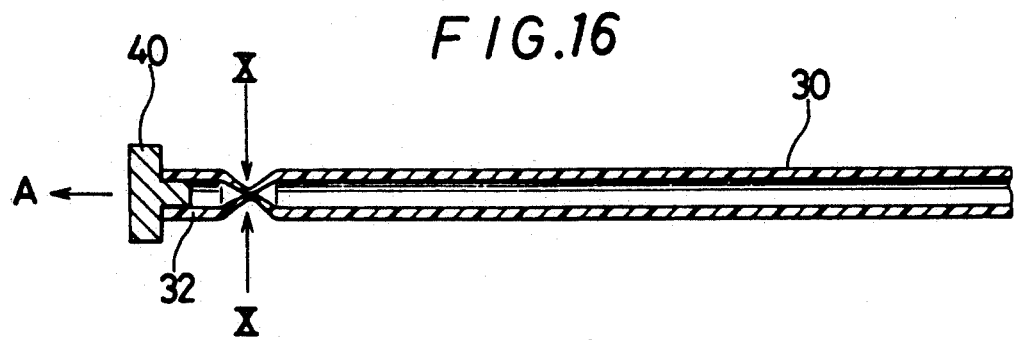
FIGS. 16, 17, 18 and 19 are explanatory views for the production steps of an expansible member in the method of producing a catheter equipped with an expansible member according to the present invention.
Figure 17:
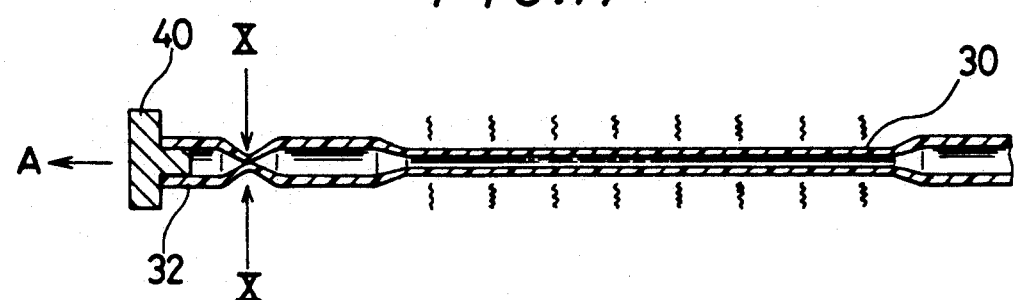
Figure 18:
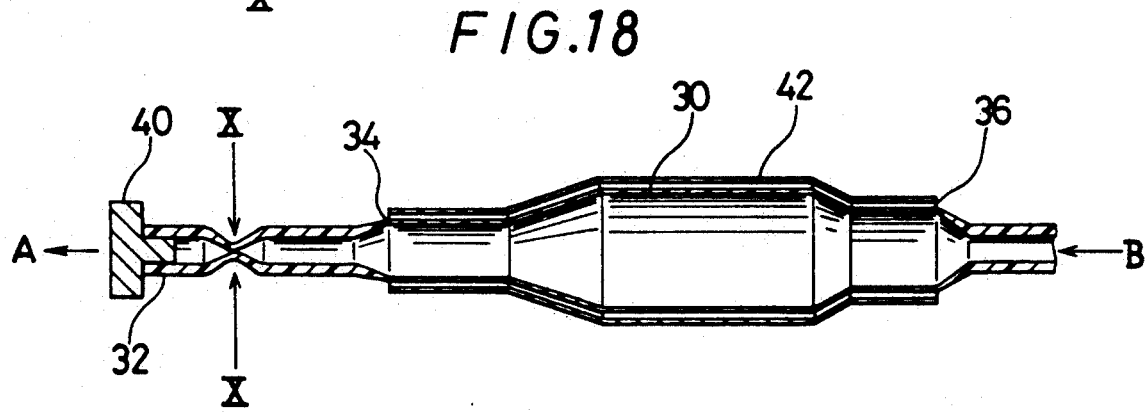

At first, as shown in FIG. 16, a tube 30 made of a thermoplastic resin is formed for forming the expansible member 3 and a tube holder 40 is attached to the end 32 of the tube 30. Further, the lumen of the tube 30 is closed at the portion X—X near the tube holder 40. The method of closing is applied by melting under heating or high frequency wave sealing or by using forceps. The tube 30 closed at the portion X—X is stretched in the direction A while applying a load to the tube holder 40, thereby removing the slackening of the tube 30. FIG. 16 shows the state in which the slackening is removed. The tube 30 removed with the slackening is heated at the portion for forming the expansible member 3 by a heating device (not illustrated) to a temperature near the melting point of the material forming the tube 30 as shown in FIG. 17. The tube 30 is maintained at the heated state, a molding die 42 the inner cavity of which is in a shape obtainable when the expansible member is inflated is fitted over the tube 30, a gas is supplied from the direction of arrow B under pressure to bring the tube 30 at the portion heated in the mold 42 into close contact with the inner wall surface of the molding die 42 as shown in FIG. 18. Then, they are left while maintaining the pressurized state till the tube 30 resumes to the normal temperature and, thereafter, the inside pressure of the tube 30 is made negative to shrink the portion as the expansible member and remove the mold 42. Then, the expansible member 3 can be formed as shown in FIG. 19 by cutting the tube 30 at the tip portion 34 and the rear end portion 36 of the tube 30. Further, if the expansible member is provided with heat shrinkability at least for the tip and the proximal portion thereof, the expansible member 3 can easily be attached to the outer tube 2 and the inner tube 1 by utilizing the heat shrinkability. At least the tip and the proximal portion of the expansible member may be provided with heat shrinkability by a method of forming the expansible member with a cross-linked thermoplastic resin or, not only restricted to such a method of using the cross-linked resin, but also by forming the expansible member in its forming step described above at such a temperature as leaving strain in the expansible member, thereby providing the expansible member with the heat shrinkability. Further, it is also possible to provide heat shrinkability by forming the expansible member in which the inner diameter at the tip thereof is somewhat smaller than the outer diameter of the inner tube and, the proximal portion is somewhat smaller than the outer diameter of the outer tube and then expanding the outer diameter of both ends of the expansible member by stretching. Then, the thus formed expansible member 3 has an outer diameter at the cylindrical portion, when it is inflated, of 1.50 to 35.00 mm, preferably, 2.00 to 30.00 mm, a length of 10.00 to 80.00 mm, preferably, 15.00 to 75.00 mm and the entire length of the expansible member 3 of 15.00 to 120.00 mm, preferably, 20.00 to 100.00 mm.

The step for forming the expansible member may be conducted at any stage, and the sequence in relation with the steps of forming the inner tube and the outer tube described above may be optional.

Further, the method of providing the expansible member according to the present invention is to be explained referring to another embodiment in conjunction with FIG. 20 through FIG. 27.

The method of producing the expansible member according to the present invention comprises a step of forming a thermoplastic resin tube and then heating expansible member forming portion of the tube, a step of disposing the heated expansible member forming portion of the tube in an expansible member molding die having the inner surface of which is formed into a shape obtainable when the expansible member is inflated, a step of bringing the heated expansible member forming portion of the tube disposed in the expansible member molding die into close contact with the inner surface of the molding die by pressurizing the inside of the tube, a step of cooling the expansible member forming portion of the tube, a step of removing the expansible member forming die from the tube and a step of cutting the molded expansible member portion off the tube.

Figure 20:
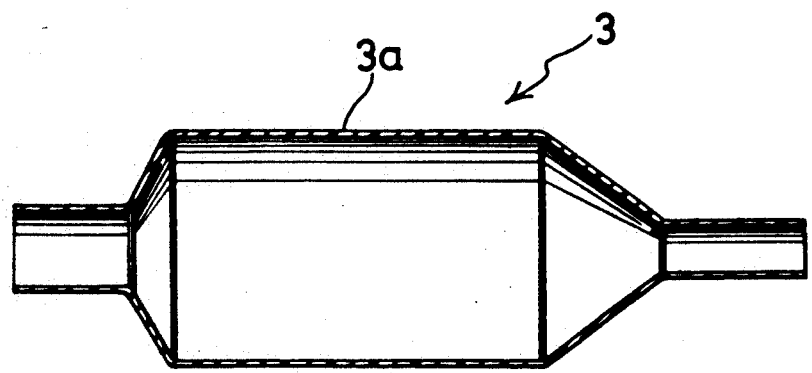
FIG. 20 is an enlarged cross sectional view for one embodiment of an expansible member produced by the method of producing the expansible member according to the present invention.

FIG. 20 is an enlarged cross sectional view for one embodiment of an expansible member produced in accordance with the present invention. The expansible member 3 is contractible or foldable and, in a state not-inflated, it can be contracted or folded. The expansible member 3 has a tip portion and a proximal portion the diameters of which are reduced respectively each in a tapered shape toward the end and has a substantially cylindrical portion 3a at least a portion of which is substantially cylindrical for easily dilatating the stricture portion of a blood vessel. The substantially cylindrical portion may not always be a complete circular cylinder but it may be a polygonal cylinder.

Figure 21:
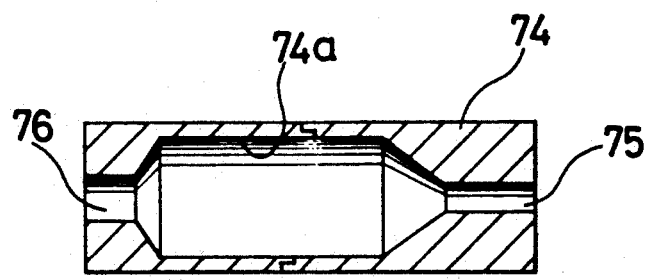
FIG. 21 is a cross sectional view of an expansible member molding die for use in the method of producing the expansible member according to the present invention.
Figure 22:
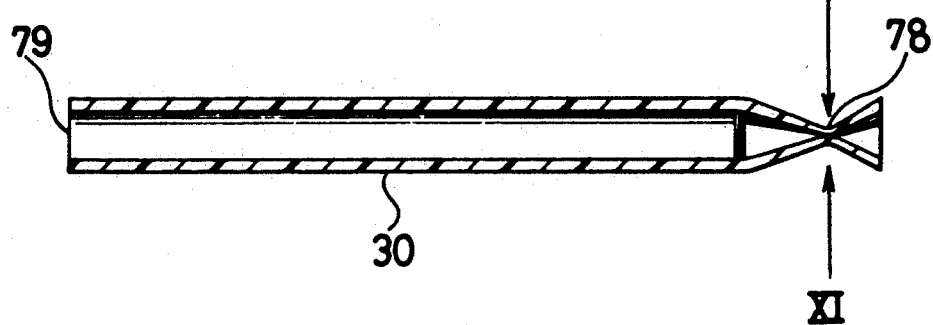
FIG. 22 is an enlarged cross sectional view of a thermoplastic resin tube used for the method of producing the expansible member according to the present invention.

FIG. 21 shows a cross sectional view of an expansible member forming die 74 used for the method of producing the expansible member according to the present invention. The expansible member molding die 74 is provided with a tip opening 75 and a base end opening 76 and has a cylindrical portion 74a for forming the substantially cylindrical portion 3a of the expansible member 3. FIG. 22 is an enlarged cross sectional view of a tube used for the method of producing the expansible member according to the present invention.

Then, explanation is to be made for each of the steps for the method of producing the expansible member according to the present invention using explanatory views for the method of producing the expansible member according to the present invention shown in FIG. 23 through FIG. 27.

A thermoplastic resin tube 30 is a tubular body opened at both ends, and the step for forming the tube 30 is conducted by using a material (preferably having flexibility), for example, thermoplastic resin such as polyolefin such as polyethylene, polypropylene, ethylene—propylene copolymer, ethylene—vinyl acetate copolymer and cross-linked ethylene—vinyl acetate copolymer, polyvinyl chloride and polyurethane, preferably, cross-linked thermoplastic resin, particularly preferably, cross-linked ethylene—vinyl acetate copolymer, by means of a known method such as extrusion molding or injection molding. Then, as the cross-linking treatment, although there may be a method of mixing a crosslinker into material for forming the tube, it is preferred to conduct by means of electron-ray irradiation or gamma-ray irradiation without using the crosslinker.

Then, before applying the step of heating the expansible member forming portion of the tube 30, one end of the tube 30 is sealed for the pressurizing step subsequently applied to the inside of the tube 30 and a pressurizing means is attached to the other end. Referring specifically, a closed portion 78 is formed by closing at the portion XI—XI at one end of the tube 30 as shown in FIG. 22. The portion XI—XI is closed by binding or heat fusing the tube. Then, as shown in FIG. 23, a pressurizing means 81 such as syringe is attached to the open end 79 of the tube 30. In this case, it is confirmed that air does not leak from the closed portion 78 and the open end 79 which is a connection portion with the pressurizing means 81 even when air is injected under pressure by the pressurizing means 81.

Further, the step of heating the expansible member forming portion of the tube is preferably applied together with a step of stretching the heated expansible member forming portion of the tube 30 in the axial direction of the tube 30. The step of stretching the heated expansible member forming portion of the tube 30 in the axial direction of the tube 30 is preferably conducted by applying a predetermined axial stretching load to the tube 30.

Referring specifically, as shown in FIG. 23, the closed portion 78 of the tube 30 is caught by a chuck 90 having a weight disk 82 attached to the tip. The expansible member molding die 74 is inserted from the tip opening 75 through the opening end 79 of the tube 30 and, subsequently, a pipe-like member such as a needle 80 having a diameter equal with or somewhat larger than the inner diameter of the tube 30 is inserted through the opening end 79, and the pressurizing means 81 such as a syringe is attached to the rear end thereof. The optimum weight of the weight 83 placed on the weight disk 82 is 132 g, for example, in a case of molding a tube made of ethylene—vinyl acetate copolymer and having 1.0 mm outer diameter and 0.45 mm inner diameter as the tube 30 and blow molding an expansible member of 2.5 mm outer diameter by using the tube partially cross-linked by means of electron-rays (geling rate of 90.4%).

Then, the step of heating the tube 30 is conducted by heating the expansible member forming portion of the tube 30 by means of a known method. Referring specifically, as shown in FIG. 24, the tube 30 is heated by using a heating device such as a heat gun (not illustrated), to heat a resin for forming the tube 30 near the melting point thereof. Then, since the end of the tube 30 is applied with a stretching load in the axial direction, the heated portion is spontaneously stretched in the heating step and, accordingly, the stretching step is applied simultaneously. If an excess load than required is applied simultaneously. If an excess load than required ia applied as the stretching load on the end of the tube 30, it goes beyond the stretching state and there is a worry that the heated portion of the tube can no more endure the weight and be disconnected. In the case of using the tube 30 with the above-mentioned conditions, it was necessary that the weight of the weight 83 is less than 190 g.

Then, explanation is to be made for the step of disposing the heated expansible member forming portion of the tube 30 is the expansible member molding die 74 the inner surface of which is in a shape obtainable when the expansible member is inflated and a step of bringing the heated expansible member forming portion of the tube 30 disposed in the expansible member molding die 74 into close contact with the inner surface of the molding die 74.

As the expansible member molding die 74, either one piece die structure or split-die structure may be used, but it is preferred in the case of using the one piece die structure that the expansible member molding die 74 is previously disposed at an optional position of the tube 30 before attaching the pressurizing means 81 to the tube 30, as shown in FIG. 23. This is not necessary in the case of using a split-type molding die.

Then, as shown in FIG. 25, the expansible member molding die 74 is set to the heated portion of the tube 30 and, subsequently, as shown in FIG. 26, the inside of the tube 30 is pressurized by the pressurizing means 81 to stretch the tube, by which the thin-walled expansible member forming portion of the tube 30 is brought into close contact with the inner surface of the molding die 74 to conduct inflation molding for the expansible member. Then, by controlling the load applied axially to the tube 30, the wall thickness of the inflation-molded expansible member 3 can be adjusted thereby enabling to produce an expansible member of constant wall thickness. In this case, it is necessary to apply a sufficient pressure by the pressurizing means 81 and blowing the heated portion of the tube 30 to surely bring it into close contact with the inner surface of the expansible member molding die 74. Then, if the stretching load applied to the tube 30 is less than the required weight, it sometimes fails to attain a predetermined thickness for the heated portion of the tube 30 and attain an expansible member of well-defined shape. In the case of using the tube 30 under the above-mentioned conditions, the required minimum load was 50 g.

Then, explanation is to be made for the step of cooling the expansible member forming portion of the tube 30, the step of removing the expansible member molding die 74 from the tube 30 and the step of cutting the expansible member portion molded to the tube 30.

At first, the step of cooling the expansible member forming portion of the tube 30 can be applied by stopping the heating for the tube 30 and allowing it to cool. Further, it may be conducted by bringing a cooling medium such as air into contact with the molding die 74. Then, the step of removing the expansible member molding die 74 from the expansible member forming portion of the tube 30 is preferably conducted by shrinking the portion of the expansible member 3 formed to the tube 30. The portion of the expansible member 3 can be shrinked by rendering the inside pressure of the tube 30 negative by the pressurizing means 31 attached to the tube 30. Further, in a case of using the split-die structure for the expansible member molding die 74, the molding die 74 may be removed by splitting and it is not always necessary to cause shrinkage to the portion of the expansible member 3. Referring more specifically, as shown in FIG. 26, after inflation molding the expansible member forming portion of the tube 30 under sufficient pressurization, it is cooled as such and, as shown in FIG. 27, the inside pressure in the expansible member and the tube is made negative by using the pressurizing means 81, thereby shrinking the expansible member forming portion and then removing the expansible member molding die from the molded expansible member 3.

If the cooling after blowing is insufficient, the molded expansible member may possibly be shrinked by the heat conducted from the heated portion of the tube 30.

The thus molded expansible member 3 is cut out at the tip portion 3b and the rear end portion 3c of the expansible member 3 from the tube 30, thereby producing the expansible member according to the present invention as shown in FIG. 20.

Figure 28:
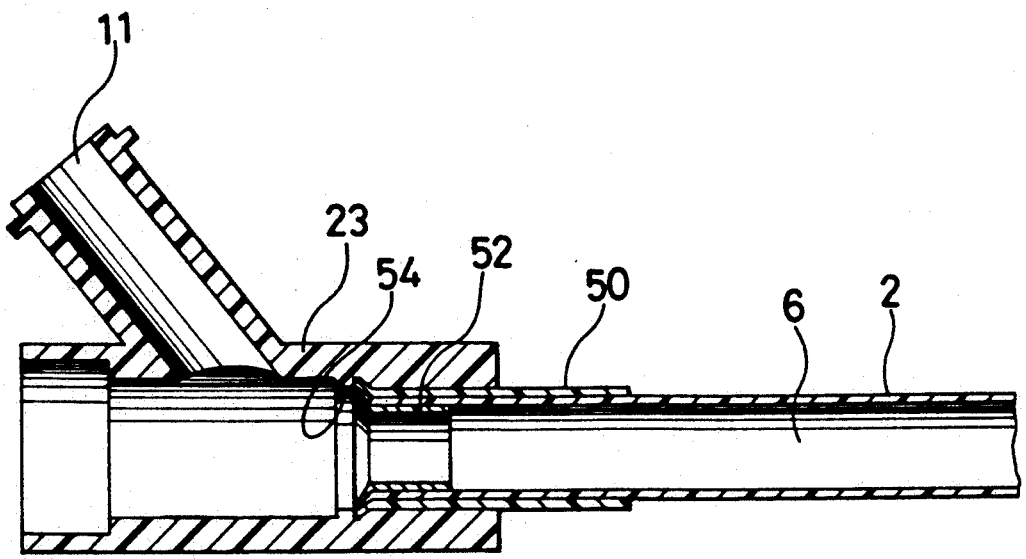
FIG. 28 is an explanatory view for the step of securing an outer tube hub to the outer tube in the method of producing a catheter equipped with an expansible member according to the present invention.

Then, explanation is to be made for the step of disposing the opening 11 to the proximal end of the outer tube 2 in communication with the lumen 6 of the outer tube. The opening 11 is preferably disposed by attaching the outer tube hub 23 having an opening to the proximal portion of the outer tube 2. Explanation is to be made for such a case as an example referring to FIG. 28.

At first, a flection-preventive tube 50 is attached to the end of the outer tube 2. The attaching can be made by a method of using a heat shrinkable tube 50 for preventing the reflexing, fitting the heat shrinkable tube 50 formed such that the inner diameter after heat shrinkage is somewhat smaller than the outer diameter of the outer tube 2 to the end of the outer tube 2, then causing it to shrink by heating (for example by exposing to hot blow). Then, the outer hub 23 is attached to the inner tube 50 is attached. Referring to the attaching method, a stopper pin 52 the outer diameter of which for the portion other than the rear end portion is substantially equal with the inner diameter of the outer tube 2 and having a rear end portion with enlarged diameter is inserted to the rear end of the outer tube 2, the outer tube 2 is inserted from its tip into the outer tube hub 23 and then enforced till the rear end of the stopper pin 52 goes beyond a protrusion 54 disposed to the inner surface of the outer tube hub 23. Further, adhesive may be coated for securing to the contact face between the outer tube hub 23 and the flection-preventive tube 50. As the material forming the outer tube hub, there can be suitably used thermoplastic resin such as polycarbonate, polyamide, polysulfon, polyarylate, methacrylate—butylene—styrene copolymer, etc.

Then, the step of forming the opening 11 in communication with the lumen 6 of the outer tube 2 at the base end portion of the outer tube 2 may be conducted at any stage so long as it is after the formation of the outer tube 2. Preferably, it is conducted after applying a step of securing the proximal portion of the expansible member 3 to the tip portion of the outer tube 2 described later. The sequence with respect to the step of forming the inner tube 1 may be optional.

Figure 29:
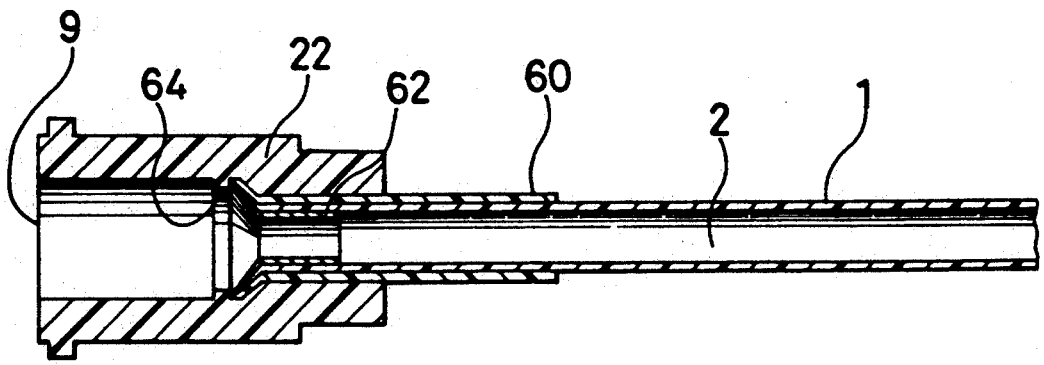
FIG. 29 is an explanatory view for the step of securing an inner tube hub to the inner tube in the method of producing a catheter equipped with an expansible member according to the present invention.

Then, explanation is to be made for the step of forming the opening 9 in communication with the lumen 4 of the inner tube 1 at the proximal portion of the inner tube 1. The opening 9 is preferably formed by attaching the inner hub 22 having the first opening 9 to the proximal portion of the outer tube 1. Explanation is to be made for such a case, as an example, referring to FIG. 29.

At first, a flection-preventive tube 52 is attached to the end of the inner tube 1. The attaching can be made by a method of using a heat shrinkable tube for the flection-preventive tube 60 fitting the heat shrinkable tube 60 formed such that the inner diameter after heat shrinkage is somewhat smaller than the outer diameter of the inner tube 1 to the end of the inner tube 1, then causing it to shrink by heating (for example by exposing to hot blow). Then, the inner tube hub 22 is attached to the inner tube 1 to which the flection-preventive tube 60 is attached. Referring to the attaching method, a stopper pin 62 the outer diameter of which for the portion other than the rear end portion is substantially equal with the inner diameter of the inner tube 1 and having a rear end portion with enlarged diameter is inserted to the rear end of the inner tube 1, the inner tube 1 is inserted from its tip into the inner tube hub 22 and then enforced till the rear end of the stopper pin 62 goes beyond a protrusion 64 disposed to the inner surface of the inner tube hub 22. Further, adhesive may be coated for securing to the contact face between the inner tube hub 22 and the flection-preventive tube 60. As the material forming the inner tube hub, there can be suitably used thermoplastic resin such as polycarbonate, polyamide, polysulfon, polyarylate, methacrylate—butylene—styrene copolymer, etc.

Then, the step of forming the opening 9 in communication with the lumen 4 of the inner tube at the proximal portion of the inner tube 1 may be conducted at any stage so long as it is after the formation of the inner tube 1. The sequence for the step of forming the outer tube 2, the step of forming the second opening 11 in communication with the lumen 6 of the outer tube 2 at the proximal portion of the outer tube 2 and a step of forming the expansible member 3 may be optional.

Then, explanation is to be made for the step of securing the proximal portion 8 of the expansible member 3 to the tip portion of the outer tube 2.

Figure 30:
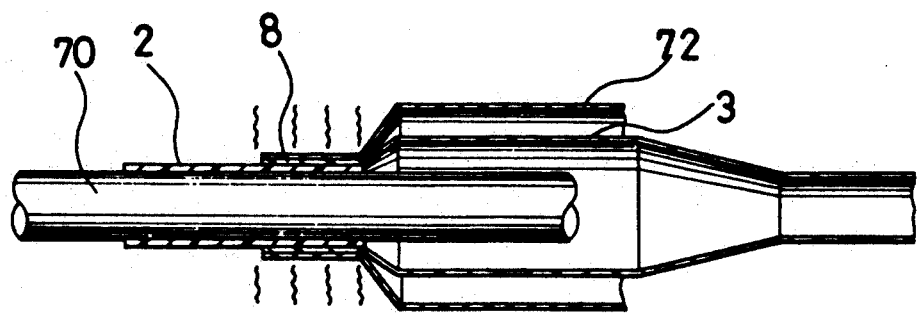
FIG. 30 is an explanatory view for the step of securing an expansible member to the outer tube in the method of producing a catheter equipped with an expansible member according to the present invention.

As the method of securing the proximal portion 8 of the expansible member 3 to the tip portion of the outer tube 2, as shown in FIG. 30, a core metal 70 having an outer diameter substantially equal with or somewhat smaller than the inner diameter of the outer tube 2 is inserted from the tip or the rear end of the outer tube 2, and the expansible member 3 is inserted from the tip portion of the core metal 70 such that the tip end of the proximal portion 8 of the expansible member coincides with the tip of the outer tube 2. Then, a glass mold 72 for bonding is fitted so as to situate over the proximal portion 8 of the expansible member 3 and the glass mold 72 is heated by a heating device (not illustrated), thereby securing the proximal portion of the expansible member 3 to the tip portion of the outer tube 2. Further, when the expansible member 3 having a heat shrinkable proximal portion 8 is used, it can easily be secured because of heat shrinkage by the heating of the glass mold 72. After securing the proximal portion 8 of the expansible member 3 to the tip portion of the outer tube 2, and then leaving the glass mold 72 till the normal temperature, the glass mold 72 is retracted from the bonded portion and the core metal 70 is drawn to easily secure the proximal portion 8 of the expansible member 3 with the tip portion of the outer tube 3.

Further, although the glass mold is used in the foregoing explanation, it is not always restricted thereto and, for example, bonding metal die may be used. Further, a high frequency transmitting electrode may be fitted to the proximal portion of the expansible member 3 by using a metal core 70, and fused by means of high frequency wave to attain securing. Furthermore, it may be fused by using the supersonic waves. The step of securing the proximal portion 8 of the expansible member 3 to the tip portion of the outer tube 2 may be conducted at any stage so long as it is after the formation of the outer tube 1 and the expansible member 3. The sequence for the step of forming the inner tube 1 and the step of forming the opening 9 in communication with the lumen 4 of the inner tube at the proximal portion of the inner tube 1 may be optional. Further, in a case of using an axially splittable die as the glass mold or metal mold and, further, in a case of securing by means of high frequency wave or supersonic wave, the sequence with respect to the step of forming the opening 11 in communication with the lumen 6 of the outer tube at the proximal portion of the outer tube 2 may be optional. In order to reduce the possibility of giving damage to the expansible member upon production, it is preferred to apply the above-mentioned step after forming the opening 11 at the proximal portion of the outer tube 2 for communication with the lumen 6 of the outer tube.

Explanation is to be made for securing the inner tube hub 22 having an opening and attached to the proximal portion of the inner tube 1 and the outer tube hub 23 attached to the proximal portion of the outer tube 1.

Figure 32:
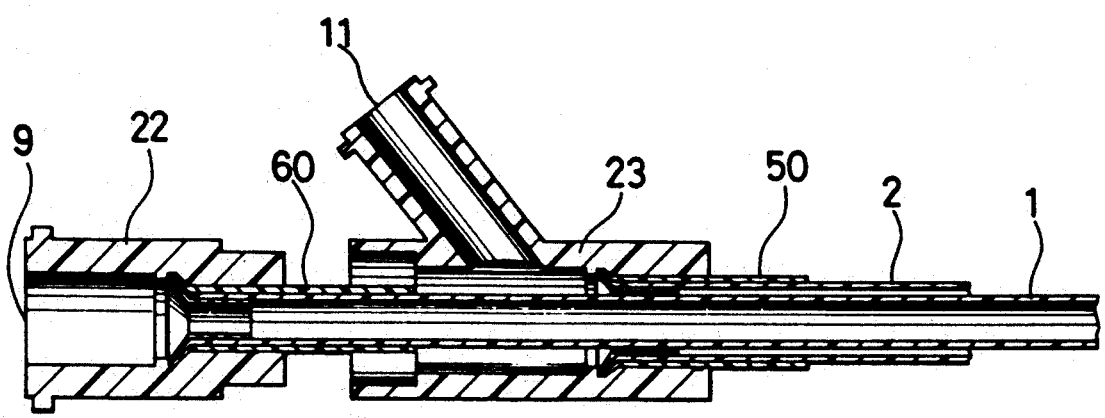
FIGS. 32 and 33 are explanatory views for the step of securing the inner tube hub and the outer tube hub in the method of producing a catheter equipped with an expansible member according to the present invention.
Figure 33:
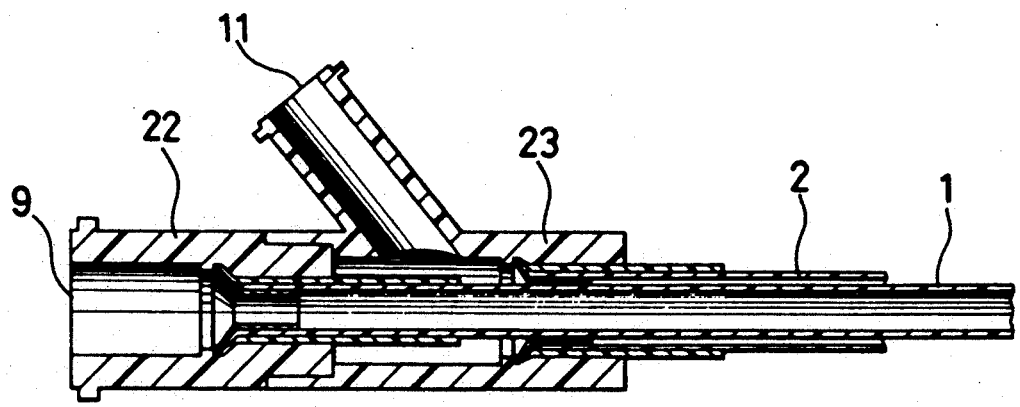

As shown in FIG. 32, the inner tube 1 is inserted from its tip from the rear end of the outer tube hub 23 attached to the proximal portion of the outer tube 2. In this instance, a core metal may be inserted to the inside of the inner tube 1 so as to prevent reflexing of the inner tube 1. Furthermore, as shown in FIG. 33, the tip portion of the inner tube hub 22 is inserted into the rear end of the outer tube hub 23 for bonding. Further, in this case, adhesive may be coated to the bonded portion between the inner tube hub 22 and the outer tube hub 23 to surely secure both of them.

The step of securing the inner tube hub 22 having an opening attached to the proximal portion of the inner tube 1 and the outer tube hub 23 attached to the proximal portion of the outer tube 1 may be applied at any time so long as it is after the application of the step of forming the inner tube 1, a step of disposing the inner tube hub 22 to the proximal portion of the inner tube 1 and, further, a step of forming the outer tube 1 and a step of disposing the outer tube hub 23 to the proximal portion. Preferably, it is applied desirably after forming the expansible member 3 and after the step of securing the expansible member 3 and the outer tube 1.

Then, explanation is to be made for the step of securing the tip portion 7 of the expansible member 3 to the tip portion of the inner tube 1.

Explanation is to be made for the step of securing the tip portion 7 of the expansible member 3 to the tip portion of the inner tube 1 referring to an example which is conducted after securing the expansible member 3 and the outer tube 1 and securing the inner tube hub 22 having an opening attached to the proximal portion of the inner tube 1 and the outer tube hub 23 attached to the proximal portion of the outer tube 1.

Figure 31:
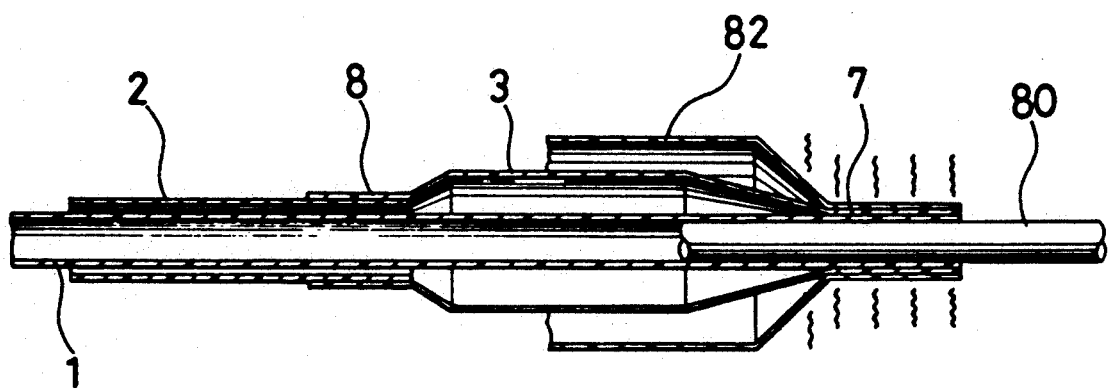
FIG. 31 is an explanatory view for the step of securing an expansible member to the inner tube in the method of producing a catheter equipped with an expansible member according to the present invention.

As shown in FIG. 31, a core metal 80 having an outer diameter substantially equal with or somewhat smaller than the inner diameter of the inner tube 1 is inserted to the inside of the inner tube 1 from the tip or the rear end of the inner tube 1. Since the expansible member 3 is secured to the outer tube 2, the inner tube 1 is inserted to the inside of the outer tube 2, and the inner tube hub 22 is secured with the outer tube hub 23, the inner tube 1 is protruded from the tip of the outer tube 2 and, further, from the tip of the expansible member 3. Then, the tip portion of the inner tube 1 protruded from the tip of the expansible member 3 is cut being aligned with the tip of the expansible member 3. Then, a bonding glass mold 82 is fitted from the tip of the core metal 80 so as to situate on the tip portion 7 of the expansible member 3 and the glass mold 82 is heated by a heating device (not illustrated) thereby securing the tip portion 7 of the expansible member 3 to the tip portion of the inner tube 1. Preferably, by using an expansible member 3 whose tip portion 7 is formed so as to be heat shrinkable, it can be secured easily because of heat shrinkage by heating from the glass mold 82. After securing the tip portion 7 of the expansible member 3 to the tip portion of the inner tube 1, and then allowing the glass mold 82 to cool to the normal temperature, glass mold is retracted from the bonded portion and the core metal 80 is withdrawn, by which the tip portion 7 of the expansible member 3 and the tip portion of the inner tube 1 can be secured with ease.

Further, although the glass mold is used in the foregoing explanation, it is not restricted only thereto but a bonding metal mold may be used for instance. Alternatively, a core metal 80 is used and an electrode for high frequency transmission may be fitted to the tip portion 7 of the expansible member 3 and securing may be conducted by fusing with high frequency wave. Furthermore, fusing may be conducted by using supersonic waves. Further, the step of securing the tip 7 of the expansible member 3 to the tip portion of the inner tube 1 is preferably conducted as the final step after securing the expansible member 3 and the outer tube 1, and after securing the inner tube hub 22 having the first opening and attached to the proximal portion of the inner tube 1 and the outer tube hub 23 attached to the proximal portion of the outer tube 1 since the production becomes easy.

The above-mentioned step may be conducted at any stage so long as it is after the formation of the inner tube 1 and the expansible member 3 in a case where an axially splittable mold is used for the glass mold or metal mold or in a case of securing by means of high frequency or supersonic wave. The sequence for the step of forming the first opening 9 in communication with the lumen 6 of the inner tube at the proximal portion of the inner tube 1, the step of forming the outer tube 2 and the step of forming the second opening 11 in communication with the lumen 6 of the outer tube at the proximal portion of the outer tube 2 may be optional.

Further, it is preferred, after securing the tip portion of the expansible member to the tip portion of the inner tube, to apply tip fabrication so as to reduce the outer diameter at the tip of the inner tube in a tapered shape toward the tip end, or so that the tip constitutes a rounded tip. The tip fabrication can easily be applied by inserting the tip of the inner tube into a mold (for example, glass mold or metal mold) having such an inner shape as conforming the aimed shape of the tip, heating the mold and then heat-deforming the tip of the inner tube along with the shape at the inside of the mold. Further, the tip of the inner tube may be fabricated by using a metal mold as the mold and applying high frequency or supersonic wave for transmission to the mold.

Then, explanation is to be made for the function of a catheter 40 having an expansible member according to the present invention using the catheter equipped with the expansible member of the embodiment shown in FIG. 1 through FIG. 5 while referring to explanatory views in FIG. 34 through FIG. 38.

Before applying dilatating cure to a stricture portion caused in a blood vessel, it is preferred that the air in the catheter equipped with the expansible member is removed as much as possible. In view of the above, suction-injection means such as a syringe is attached to the second opening 11 of the catheter according to the present invention, liquid (vasodiographic contrast liquid, etc.) is charged in the cylinder and suction and injection are repeated, so that the air in the second lumen and the expansible member is removed and replaced with the liquid.

Figure 34:
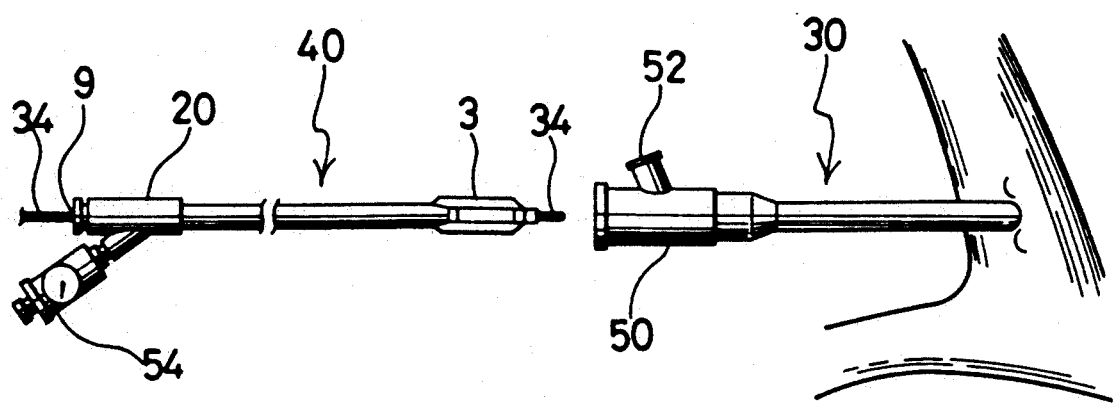
FIGS. 34, 35, 36, 37 and 38 are respectively explanatory views for illustrating the function of the catheter equipped with the expansible member according to the present invention.
Figure 35:
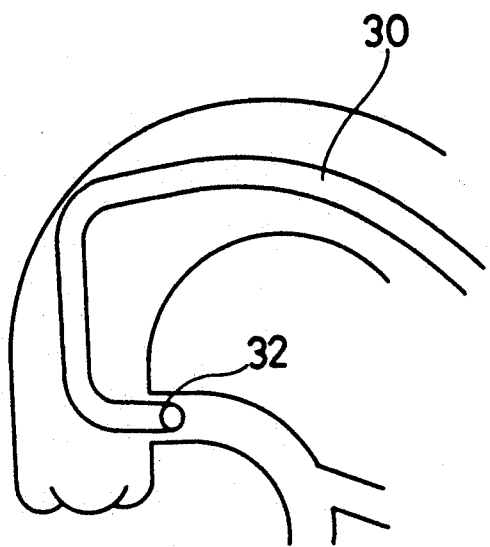
Figure 36:
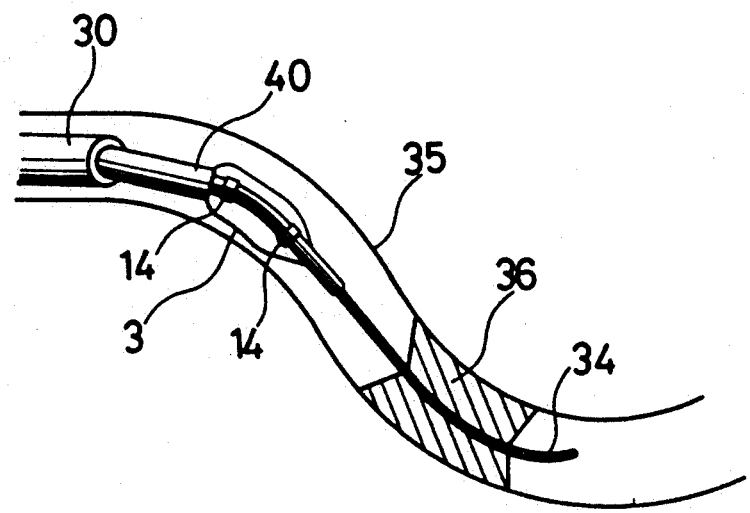
Figure 37:
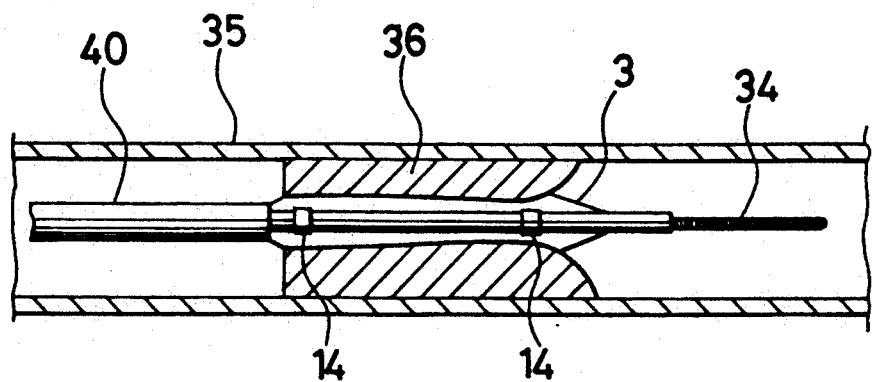
Figure 38:
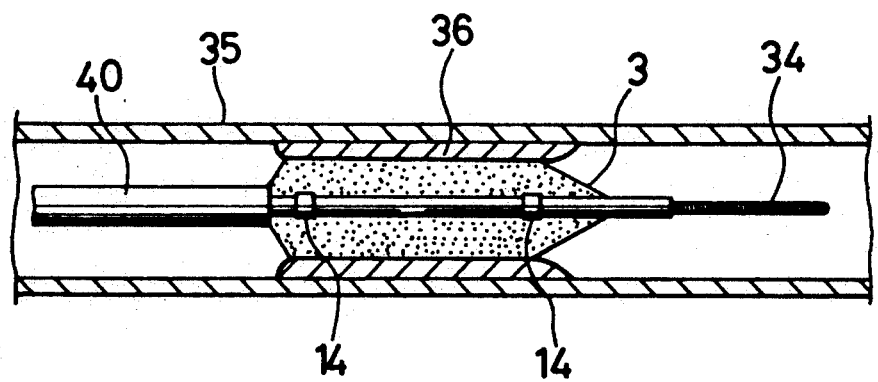

Then, upon inserting the catheter 40 with the expansible member into a human body, a blood vessel is secured in the human body by means of Seldinger method, etc., then a guide wire for guide catheter (not illustrated) is retained in the blood vessel, the guide catheter is inserted therealong into the blood vessel and, as shown in FIG. 35, the guide catheter 30 is retained at the inlet 32 of coronary artery having aimed lesion part. Then, the guide wire for the guide catheter is withdrawn. As shown in FIG. 34, the catheter 40 equipped with the expansible member according to the present invention having the guide wire 34 for the catheter equipped with the expansible member inserted therethrough is inserted by means of the Y-shaped connector 50 disposed at the rear end of the guide catheter 30. Insertion into the blood vessel is conducted in a state where the guide wire 34 for the catheter equipped with the expansible member is protruded by several centimeters from the tip of the catheter 40 equipped with the expansible member. The catheter 40 equipped with the expansible member advances in the guide catheter 30 and, as shown in FIG. 36, leaves the tip of the guide catheter 30 and enters the blood vessel 35 having the aimed lesion part. Subsequently, the guide wire 34 for the catheter equipped with the expansible member is advanced to the aimed lesion part, passed through the stricture portion 36 and then retained. The catheter 40 equipped with the expansible member is advanced in the blood vessel 35 along the guide wire 34 for the catheter equipped with the expansible member. After the catheter 40 equipped with the expansible member has reached a position near the stricture portion 36, the expansible member 3 is situated in the stricture portion 36 under X-ray perspection by using X-ray impermeable markers 14 disposed on the inner tube as the reference marks as shown in FIG. 37. Subsequently, vasodiographic contrast liquid is injected at a pressure from several atm. to ten and several atm. by means of an injector 54 equipped with a pressure gauge connected to the second opening forming the injection port of the catheter 40 equipped with the expansible member as shown in FIG. 34, thereby compressing and dilatating the stricture portion 36 as shown in FIG. 38. Then, the expansible member 3 is caused to shrink and retract from the stricture portion 36 of the dilatated blood vessel. Then, the vasodiographic contrast liquid is injected through the contrast liquid injection port 52 of the Y-shaped connector 50 of the guide catheter 30 shown in FIG. 34 to confirm the state of blood stream at the peripheral side. When improvement of the blood stream at the peripheral side is recognized, the catheter 40 equipped with the expansible member and the guide wire 34 for the catheter equipped with the expansible member are withdrawn and, thereafter, the guide catheter is withdrawn and blood is stopped under pressure to complete the operation.

INDUSTRIAL APPLICABILITY

Since the catheter equipped with the expansible member according to the present invention comprises an inner tube having a first lumen whose tip is open, an outer tube disposed coaxially with the inner tube, having the tip thereof at a position recessed by a predetermined length from the tip of the inner tube and forming a second lumen between it and the outer surface of the inner tube, a contractible or foldable expansible member having a tip portion and a proximal portion in which the proximal portion is fitted to the outer tube and the tip portion is fitted to the inner tube, and communicating with the second lumen near the proximal portion, a first opening communicating with the first lumen disposed at the base end portion of the inner tube, a second opening communicating with the second lumen disposed at the proximal portion of the outer tube, and a rigidity imparting member disposed in at least one of the inner and the outer tubes so as to extend in an axial direction and, particularly, it comprises the rigidity imparting member, there is no worry that the catheter is reflexed during insertion into a blood vessel and, further, torque and enforcing force can reliably be transmitted to the tip by displacing, rotating or enforcing the catheter in a delicate manner at the proximal portion of the catheter in a case where the tip of the catheter is displaced or rotated in a delicate manner, thereby providing excellent operationability. Further, since the second lumen in communication near the proximal portion of the expansible member and to which the inflating fluid for the expansible member is charged is formed between the inner tube and the outer tube, it has a relatively large volume and, accordingly, the inflating fluid can easily be charged even if it has high flow resistance such as the basodiographic contrast liquid.

Since the method of producing a catheter equipped with an expansible member according to the present invention comprises a step of forming an inner tube having a lumen opened from the tip to the rear end, a step of forming an outer tube having a lumen opened from the tip to the rear end, having an inner diameter greater than the outer diameter of the inner tube and shorter by a predetermined length than the inner tube, a step of forming a contractible or foldable expansible member having a tip portion and a proximal portion, a step of inserting the inner tube into the outer tube, a step of securing the proximal portion of the expansible member to the tip portion of the outer tube, and a step of securing the tip portion of the expansible member to the tip portion of the inner tube and particularly, since the expansible member is formed separately, the length and the wall thickness of the expansible member can be made optionally. Further, since the inner tube and the outer tube are independent of each other, there is no requirement for providing a complicate step of inserting and securing a narrow extending tube into either one of the lumens with small inner diameter as in the case of producing a catheter of double lumen type equipped with an expansible member, and the catheter equipped with the expansible member can be produced with ease.

Since the method of producing the expansible member according to the present invention concerns a method of producing an expansible member used for the catheter equipped with the expansible member, which comprises a step of molding a thermoplastic resin tube and then heating the expansible member forming portion of the tube, a step of disposing the heated expansible member forming portion of the tube into an expansible member molding die the inner surface of which is in such a shape as obtainable when the expansible member is inflated, a step of pressurizing the inside of the tube thereby bringing the heated expansible member forming portion of the tube disposed in the expansible member molding die in close contact with the inner surface of the molding die, a step of cooling the expansible member forming portion of the tube, a step of removing the expansible member molding die from the tube and a step of cutting the expansible member portion formed to the tube and, particularly, since inflation molding is applied in the expansible member molding die the inner surface of which is in such a shape as obtainable when the expansible member is inflated, the length and the thickness of the expansible member can be made uniform and, accordingly, an expansible member of high reproducibility for the outer diameter of the expansible member upon inflation can easily be produced.

We claim:

1. A catheter equipped with an expansible member, comprising:
    an inner tube having a first lumen, said inner tube having an open tip at an end portion thereof;
    an outer tube disposed coaxially with said inner tube, said outer tube having a tip portion at a position recessed by a predetermined distance from the tip of said inner tube, and forming a second lumen between said outer tube and an outer surface of said inner tube;
    a contractible or foldable expansible member having:
        a tip portion connected to said inner tube; and
        a proximal portion connected to said outer tube; and
    said expansible member communicating with said second lumen near said proximal portion of said expansible member, and said expansible member surrounding a distal end portion of said inner tube which is not surrounded by said outer tube;
    a first opening communicating with said first lumen, said first opening being disposed at a proximal end portion of said inner tube;
    a second opening communicating with said second lumen, said second opening being disposed at a proximal end portion of said outer tube; and
    a rigidity imparting member disposed in or on only said inner tube so as to extend from a proximal end portion of said inner tube to a position of said inner tube in the vicinity of the tip portion of said outer tube without extending along said distal end portion of said inner tube which is surrounded by said expansible member, and said rigidity imparting member comprising a wire mesh-like material.

2. A catheter equipped with an expansible member according to claim 1, further comprising a branched hub attached to the proximal ends of each inner tube and said outer tube, and wherein said first opening and said second opening are disposed at said branched hub.

3. A catheter equipped with an expansible member according to claim 1, wherein the tip of said inner tube comprises an annular member attached to said tip end portion of said inner tube.

4. A catheter equipped with an expansible member according to claim 1, wherein said rigidity imparting member is embedded in the inside of said inner tube.

5. A catheter equipped with an expansible member according to claim 1, wherein said rigidity imparting member is embedded in the outer surface of said inner tube.

6. A catheter equipped with an expansible member according to claim 1, wherein said wire material comprises metal wire.

7. A catheter equipped with an expansible member according to claim 1, wherein said wire material comprises synthetic fibers.

8. A catheter equipped with an expansible member according to claim 7, wherein said synthetic fibers are any one of polyamide fibers, polyester fibers and polypropylene fibers.

9. A catheter equipped with an expansible member according to claim 1, wherein an outer surface of said outer tube and an outer surface of said expansible member having a hydrophilic material thereon so that said surfaces have lubricancy.

10. A method of producing a catheter equipped with an expansible member, comprising the steps of:
    providing an inner tube having a lumen which is opened from a tip of said inner tube to a rear end portion of said inner tube;
    disposing a rigidity imparting member comprised of a wire mesh-like material only to said inner tube so as to extend from a proximal end of said inner tube to a portion of said inner tube spaced from the tip of said inner tube so as to form a distal end portion of said inner tube not provided with said rigidity imparting member;
    providing an outer tube having a lumen which is opened from a distal tip of said outer tube to a proximal end of said outer tube, said outer tube having an inner diameter larger than the outer diameter of said inner tube, and said outer tube being shorter by a predetermined length than said inner tube so that said tip of said outer tube does not extend to the tip of said inner tube;
    providing a contractible or foldable expansible member having a tip portion and a proximal portion;
    inserting said inner tube into the inside of said outer tube such that the tip of the inner tube extends past the tip of the outer tube;
    securing said proximal portion of said expansible member to a tip end portion of said outer tube; and
    securing said tip portion of said expansible member to a tip end portion of said inner tube, whereby said expansible member surrounds a portion of said inner tube which extends past said outer tube and which is not provided with said rigidity imparting member.

11. A method of producing a catheter equipped with an expansible member according to claim 10, wherein said step of disposing said rigidity imparting member to said inner tube comprises:
    applying said rigidity imparting member to said inner tube; and then
    embedding the thus applied rigidity imparting member into said inner tube.

12. A method of producing a catheter equipped with an expansible member according to claim 10, wherein said step of securing said tip portion of said expansible member to said tip end portion of said inner tube is conducted after securing said proximal portion of said expansible member to said tip end portion of said outer tube and ten inserting said inner tube into said outer tube secured with said expansible member.

13. A method of producing a catheter equipped with an expansible member according to claim 10, wherein said step of securing said tip portion of said expansible member to said tip end portion of said inner tube comprises securing said tip portion of said expansible member by heat shrinkage under heating.

14. A method of producing a catheter equipped with an expansible member according to claim 10, wherein said step of securing said tip portion of said expansible member to said tip end portion of said inner tube comprises securing said proximal portion of said expansible member by heat shrinkage under heating.

15. A method of producing a catheter equipped with an expansible member according to claim 10, further comprising a step of forming an opening at the proximal portion of said inner tube in communication with said lumen of said inner tube and a step of forming an opening at the proximal portion of said outer tube in communication with said lumen of said outer tube.

16. A catheter equipped with an expansible member, comprising:
an inner tube having a first lumen, said inner tube having an open tip at an end portion thereof;
an outer tube disposed coaxially with said inner tube, said outer tube having a tip portion at a position recessed by a predetermined distance from the tip of said inner tube, and forming a second lumen between said outer tube and an outer surface of said inner tube;
a contractible or foldable expansible member having a tip portion connected to said inner tube and a proximal portion connected to said outer tube, said expansible member communicating with said second lumen near said proximal portion of said expansible member and surrounding said inner tube over a given length of said inner tube, and said expansible member being made of a material selected from the group consisting of polyolefin, polyvinyl chloride, polyamide elastomer and polyester;
a first opening communicating with said first lumen, said first opening being disposed at a proximal end portion of said inner tube;
a second opening communicating with said second lumen, said second opening being disposed at a proximal end portion of said outer tube, and
a rigidity imparting member disposed in or on only said inner tube, said rigidity imparting member extending in the axial direction of said inner tube.

17. A catheter equipped with an expansible member according to claim 16, further comprising a branched hub attached to the proximal ends of said inner tube and said outer tube, and wherein said first opening and said second opening are disposed at said branched hub.

18. A catheter equipped with an expansible member according to claim 16, wherein the tip portion of said inner tube does not have said rigidity imparting member disposed therein, and said rigidity imparting member is formed with an annular member disposed at the vicinity of the tip of said outer tube.

19. A catheter equipped with an expansible member according to claim 18, wherein said rigidity imparting member is provided at least from said proximal portion of said inner tube to the portion of said inner tube surrounded by said expansible member.

20. A catheter equipped with an expansible member according to claim 16, wherein the tip of said inner tube is formed with an annular member attached to said tip of said inner tube at a portion of said inner tube not having said rigidity imparting member.

21. A catheter equipped with an expansible member according to claim 16, wherein, said rigidity imparting member is embedded in the inside of said inner tube.

22. A catheter equipped with an expansible member according to claim 16, wherein said rigidity imparting member is embedded in the outer surface of said inner tube.

23. A catheter equipped with an expansible member according to claim 16, wherein said rigidity imparting member comprises a wire mesh-like material.

24. A catheter equipped with an expansible member according to claim 23, wherein said wire mesh-like material comprises metal wire.

25. A catheter equipped with an expansible member according to claim 23, wherein said wire mesh-like material comprises synthetic fibers.

26. A catheter equipped with an expansible member according to claim 16, wherein said expansible member comprises a substantially cylindrical portion having a substantially constant diameter along the length thereof.

27. A catheter equipped with an expansible member according to claim 26, wherein a distal and a proximal portion of said cylindrical portion of said expansible member are tapered.

28. A catheter equipped with an expansible member according to claim 16, wherein said polyolefin is a material selected from the group consisting of polyethylene, polypropylene, ethylene-vinyl acetate copolymer or cross-linked ethylene-vinyl acetate copolymer.

* * * * *